(12) United States Patent
Sun et al.

(10) Patent No.: US 11,141,391 B2
(45) Date of Patent: Oct. 12, 2021

(54) BIOMARKERS FOR RISK ASSESSMENT, DIAGNOSIS AND TARGET MICROBIOME AND INTESTINAL HOMEOSTASIS FOR PREVENTION AND TREATMENT OF AMYOTROPHIC LATERAL SCLEROSIS

(71) Applicant: Rush University Medical Center, Chicago, IL (US)

(72) Inventors: Jun Sun, Chicago, IL (US); Jingsong Zhou, Chicago, IL (US); Shaoping Wu, River Forest, IL (US); Jianxun Yi, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 35 days.

(21) Appl. No.: 15/310,294

(22) PCT Filed: May 11, 2015

(86) PCT No.: PCT/US2015/030109
§ 371 (c)(1),
(2) Date: Nov. 10, 2016

(87) PCT Pub. No.: WO2015/175388
PCT Pub. Date: Nov. 19, 2015

(65) Prior Publication Data
US 2017/0296494 A1 Oct. 19, 2017

Related U.S. Application Data

(60) Provisional application No. 61/992,007, filed on May 12, 2014.

(51) Int. Cl.
| | | |
|---|---|---|
| *C12Q 1/04* | (2006.01) | |
| *C12Q 1/6883* | (2018.01) | |
| *C12Q 1/689* | (2018.01) | |
| *G01N 33/50* | (2006.01) | |
| *G01N 33/68* | (2006.01) | |
| *A61K 31/19* | (2006.01) | |
| *C12N 9/10* | (2006.01) | |
| *C07K 14/47* | (2006.01) | |
| *C07K 14/705* | (2006.01) | |
| *A61K 9/00* | (2006.01) | |

(52) U.S. Cl.
CPC ............ *A61K 31/19* (2013.01); *A61K 9/0053* (2013.01); *C07K 14/4723* (2013.01); *C07K 14/705* (2013.01); *C12N 9/13* (2013.01); *C12Q 1/04* (2013.01); *C12Q 1/689* (2013.01); *C12Q 1/6883* (2013.01); *C12Y 208/03008* (2013.01); *G01N 33/5091* (2013.01); *G01N 33/6896* (2013.01); *C12Q 2600/118* (2013.01); *C12Q 2600/156* (2013.01); *C12Q 2600/158* (2013.01); *G01N 2333/46* (2013.01); *G01N 2800/285* (2013.01); *G01N 2800/2835* (2013.01); *G01N 2800/50* (2013.01); *Y02A 50/30* (2018.01)

(58) Field of Classification Search
CPC ........ A61K 31/19; A61K 9/0053; C12Q 1/04; C12Q 1/6883; C12Q 1/689; C12Q 2600/118; C12Q 2600/156; C12Q 2600/158; C07Q 14/705; C07Q 14/4723; G01N 33/5091; G01N 33/6896; G01N 2800/2835; G01N 2800/50
See application file for complete search history.

(56) References Cited

U.S. PATENT DOCUMENTS

| 5,935,799 A | 8/1999 | Isbister |
|---|---|---|
| 2006/0135612 A1 | 6/2006 | Ferrante |
| 2009/0305267 A1* | 12/2009 | Krause ..................... C12Q 1/37 435/6.17 |
| 2013/0267469 A1 | 10/2013 | Matson |

FOREIGN PATENT DOCUMENTS

| CN | 102183651 A | 9/2011 |
|---|---|---|
| WO | WO 2013/050792 A1 | 4/2013 |
| WO | WO 2013/155365 * | 4/2013 |
| WO | WO 2013/148709 A1 | 10/2013 |
| WO | WO 2013/155365 A1 | 10/2013 |

OTHER PUBLICATIONS

Kumar et al., Journal of Biomarkers, vol. 2013, Article ID 538765, 15 pages.*
Longstreth et al., Medical Hypotheses (2005) 64, 1153-1156.*
Radu et al., Mediators of Inflammation, 2013, vol. 2013, pp. 1-19.*
Mastroianni et al., J. Biol. Chem. vol. 284, No. 41, pp. 27848-27856, Oct. 9, 2009.*
Finegold et al., Clinical Infectious Diseases 2002; 35(Suppl 1):S6-16.*
Liu et al, 2013, "Microbial Products Induce Claudin-2 to Compromise Gut Epithelial Barrier Function" PLoS ONE 8(8):e68547 (Year: 2013).*
Louis et al., Applied and Environmental Microbiology, Mar. 2007, vol. 73, No. 6, p. 2009-2012 (Year: 2012).*
Shifflett et al., "Enteropathogenic *E. coli* disrupts tight junction barrier function and structure in vivo", Laboratory Investigation, 2005, 85: 1308-1324 (Year: 2005).*
O'Neil et al., "Expression and Regulation of the Human beta Defensins hBD-1 and hBD-2 in Intestinal Epithelium", J Immunology, 1999, 163: 6718-6724 (Year: 1999).*

(Continued)

*Primary Examiner* — Ruth A Davis
(74) *Attorney, Agent, or Firm* — Barnes & Thornburg LLP

(57) ABSTRACT

Methods of selecting a subject for treatment of amyotrophic lateral sclerosis (ALS) and methods of treatment for subjects having ALS or at risk of developing ALS are provided. The method of selecting subjects for treatment includes obtaining a biological sample from the subject, where the sample is obtained from the subject's gastrointestinal tract or skeletal muscle. The method further includes measuring a biomarker in the subject's sample and selecting the subject for treatment of ALS when the biomarker measurement in the subject's sample is lower or higher relative to a control measurement.

14 Claims, 9 Drawing Sheets

Specification includes a Sequence Listing.

(56) References Cited

OTHER PUBLICATIONS

Kinugasa et al., "Claudins Regulate the Intestinal Barrier in Response to Immune Mediators", Gastroenterology, 2000, 118: 1001-1011 (Year: 2000).*

Vaishnava et al, "Paneth cells directly sense gut commensals and maintain homeostasis at the intestinal host-microbial interface", PNAS, Dec. 2008, vol. 105, No. 52, p. 20858-20863 (Year: 2008).*

Adhihetty, P.J. et al.; "Effect of denervation on mitochondrially mediated apoptosis in skeletal muscle"; Journal of Applied Physiology, vol. 102; pp. 1143-1151; Mar. 1, 2007.

Alonso, A. et al.; "Incidence and lifetime risk of motor neuron disease in the United Kingdom: a population-based study"; European Journal of Neurology, vol. 16; pp. 745-751; Jun. 2009.

Banerjee, R. et al.; "Autophagy in neurodegenerative disorders: pathogenic roles and therapeutic implications"; Trends in Neurosciences, vol. 33, No. 12; pp. 541-549; Dec. 2010.

Bhattacharya, A. et al.; "Dietary restriction but not rapamycin extends disease onset and survival of the H46R/H48Q mouse model of ALS"; Neurobiology of Aging, vol. 33; pp. 1829-1832; Aug. 31, 2012.

Blikslager, A. T. et al.; "Restoration of barrier function in injured intestinal mucosa"; Physiological Reviews, vol. 87; pp. 545-564; Apr. 1, 2007.

Boillée, S. et al.; "ALS: a disease of motor neurons and their nonneuronal neighbors"; Neuron, vol. 52; pp. 39-59; Oct. 5, 2006.

Boncompagni, S. et al.; "Mitochondria are linked to calcium stores in striated muscle by developmentally regulated tethering structures"; Molecular Biology Cell, vol. 20; pp. 1058-1067; Feb. 1, 2009.

Bové, J. et al.; "Fighting neurodegeneration with rapamycin: mechanistic insights"; Nature Reviews Neuroscience, vol. 12; pp. 437-452; Aug. 2011.

Cadwell, K. et al.; "A unique role for autophagy and the Atg16L1 in Paneth cells in murine and human intestine"; Nature; pp. 259-263; Nov. 2008.

Chen, S. et al.; "Autophagy dysregulation in amyotrophic lateral sclerosis"; Brain Pathology, vol. 22; pp. 110-116; Jan. 2012.

Collins, S. M. et al.; "The relationship between intestinal microbiota and the central nervous system in normal gastrointestinal function and disease"; Gastroenterology, vol. 136; pp. 2003-2014; May 13, 2009.

Crippa, V. et al.; "Differential autophagy power in the spinal cord and muscle of transgenic ALS mice"; Frontiers in Cellular Neuroscience, vol. 7, Article 234; Nov. 2013.

Deng, H. X. et al.; "Conversion to the amyotrophic lateral sclerosis phenotype is associated with intermolecular linked insoluble aggregates of SOD1 in mitochondria"; Proceedings of the National Academy of Sciences, 103; pp. 7142-7147; May 2, 2006.

Díaz-Troya, S. et al.; "The role of TOR in autophagy regulation from yeast to plants and mammals"; Autophagy, vol. 4; pp. 851-865; Oct. 1, 2008.

Djavaheri-Mergny, M. et al.; "Cross talk between apoptosis and autophagy by caspase-mediated cleavage of Beclin 1"; Oncogene vol. 29; pp. 1717-1719; Jan. 25, 2010.

Dobrowolny, G. et al.; "Muscle atrophy induced by SOD1G93A expression does not involve the activation of caspase in the absence of denervation"; Skeletal Muscle, vol. 1, Issue 3; Jan. 24, 2011.

Dobrowolny, G. et al.; "Skeletal muscle is a primary target of SOD1G93A-mediated toxicity"; Cell Metabolism, vol. 8; pp. 425-436; Nov. 5, 2008.

Dobrowolny, G. et al.; "Muscle expression of a local Igf-1 isoform protects motor neurons in an ALS mouse model"; The Journal of Cell Biology, vol. 168; pp. 193-199; Jan. 17, 2005.

Farhadi, A. et al.; "Intestinal barrier: an interface between health and disease"; Journal of Gastroenterolical Hepatology, vol. 18; pp. 479-497; May 1, 2003.

Finegold, S. M. et al.; "Pyrosequencing study of fecal microflora of autistic and control children" Anaerobe, vol. 16; pp. 444-453; Aug. 31, 2010.

Fornai, F. et al.;"Lithium delays progression of amyotrophic lateral sclerosis"; Procedures of the National Academy of Sciences,105; pp. 2052-2057; Feb. 12, 2008.

Frey, D. et al.; "Early and selective loss of neuromuscular synapse subtypes with low sprouting competence in motoneuron diseases"; The Journal of Neuroscience, vol. 20; pp. 2534-2542; Apr. 1, 2000.

Fung et al.; "A review of the potential mechanisms for the lowering of colorectal oncogenesis by butyrate"; British Journal of Nutrition, vol. 108; pp. 820-831; Sep. 14, 2012.

Grumati, P.et al.; "Autophagy is defective in collagen VI muscular dystrophies, and its reactivation rescues myofiber degeneration"; Nature Medecine, vol. 16, No. 11; pp. 1313-1320; Nov. 2010.

Guégan, C. et al.; "Recruitment of the Mitochondrial-Dependent Apoptotic Pathway in Amyotrophic Lateral Sclerosis"; The Journal of Neuroscience, vol. 21; pp. 6569-6576; Sep. 1, 2001.

Gurney, M.E. et al.; "Motor neuron degeneration in mice that express a human Cu,Zn superoxide dismutase mutation"; Science, vol. 264; pp. 1772-1775; Jun. 17, 1994.

Hakansson, A. et al.; "Gut Microbiota and Inflammation"; Nutrients, vol. 3; pp. 637-682; Jun. 1, 2011.

Hetz, C. et al.; "XBP-1 deficiency in the nervous system protects against amyotrophic lateral sclerosis by increasing autophagy"; Genes & Development, vol. 23; pp. 2294-2306; Oct. 2009.

Hooper, L.V.; "Do symbiotic bacteria subvert host immunity?"; Nature Reviews Microbiology, vol. 7; pp. 367-374; May 2009.

Hooper, L.V. et al.; "How Host-Microbial Interactions Shape the Nutrient Environment of the Mammalian Intestine"; Annual Review of Nutrition, vol. 22; pp. 283-307; Jul. 2002.

Hsiao, E. Y. et al.; "Microbiota modulate behavioral and physiological abnormalities associated with neurodevelopmental disorders"; Cell, vol. 155; pp. 1451-1463; Dec. 19, 2013.

Ikenaka, K. et al.; "dnc-1/dynactin 1 knockdown disrupts transport of autophagosomes and induces motor neuron degeneration" PloS One 8, No. 2; e54511; 18 pages; Feb. 7, 2013.

Ivanova, M. I. et al.; "Aggregation-triggering segments of SOD1 fibril formation support a common pathway for familial and sporadic ALS"; Proceedings of the National Academy Sciences, vol. 111, No. 1; pp. 197-201; Jan. 7, 2014.

Joyce, P.I. et al.; "SOD1 and TDP-43 animal models of amyotrophic lateral sclerosis: recent advances in understanding disease toward the development of clinical treatments"; Mamm Genome, vol. 22, Issue 7; pp. 420-448; Aug. 2011.

Ju, J.-S.; "Quantitation of 'autophagic flux' in mature skeletal muscle"; Autophagy, vol. 6; pp. 929-935; Oct. 1, 2010.

Kabeya, Y. et al.; "LC3, a mammalian homologue of yeast Apg8p, is localized in autophagosome membranes after processing"; The EMBO Journal, vol. 19; pp. 5720-5728; Nov. 1, 2000.

Kaspar, B.K. et al.; "Retrograde Viral Delivery of IGF-1 Prolongs Survival in a Mouse ALS Model"; Science, vol. 301; pp. 839-842; Aug. 8, 2003.

Kim, J. et al.; "Dimerization, oligomerization, and aggregation of human amyotrophic lateral sclerosis Cu/Zn-superoxide dismutase 1 mutant forms in live cells"; Journal of Biological Chemistry, vol. 289, No. 21; pp. 15094-15103; May 23, 2014.

Klionsky, D.J. et al.; "Guidelines for the use and interpretation of assays for monitoring autophagy in higher eukaryotes"; Autophagy, vol. 4: pp. 151-175; Feb. 16, 2008.

Laukoetter, M. G. et al.; "JAM-A regulates permeability and inflammation in the intestine in vivo"; The Journal of Experimental Medicine, vol. 204, No. 13; pp. 3067-3076; Dec. 24, 2007.

Lee, H. E. et al.; "Delineating the relationships among the formation of reactive oxygen species, cell membrane instability and innate autoimmunity in intestinal reperfusion injury"; Molecular Immunology, vol. 58, No. 2; pp. 151-159; Apr. 30, 2014.

Li, L. et al.; "Altered macroautophagy in the spinal cord of SOD1 mutant mice"; Autophagy, vol. 4; pp. 290-293; Apr. 1, 2008.

Ling, J. et al.; "Structural constraints for the binding of short peptides to claudin-4 revealed by surface plasmon resonance"; Journal of Biological Chemistry, vol. 283, No. 45; pp. 30585-30595; Nov. 7, 2008.

Littman, D.R. et al.; Role of the Commensal Microbiota in Normal and Pathogenic Host Immune Responses; Cell Host & Microbe, vol. 10, Issue 4; pp. 311-323; Oct. 20, 2011.

(56) References Cited

OTHER PUBLICATIONS

Lu R. et al.; "Chronic Effects of a *Salmonella* Type III Secretion Effector Protein AvrA In Vivo"; PLoS One, vol. 5, Issue 5; e10505; 13 pages; May 2010.
Luo, S. et al.; "Apoptosis blocks Beclin 1-dependent autophagosome synthesis: an effect rescued by Bcl-xL"; Cell Death & Differentiation, vol. 17; pp. 268-277; Feb. 1, 2010.
Luo, G. et al.; "Defective mitochondrial dynamics is an early event in skeletal muscle of an amyotrophic lateral sclerosis mouse model" PloS One, vol. 8, Issue 12; e82112; ten pages; Dec. 2013.
Maes, M. et al.; "The gut-brain barrier in major depression: intestinal mucosal dysfunction with an increased translocation of LPS from gram negative enterobacteria (leaky gut) plays a role in the inflammatory pathophysiology of depression"; Neuroendocrinology Letters, vol. 29, No. 1; pp. 117-124. Feb. 1, 2008.
Maiuri, M.C. et al.; "Crosstalk between apoptosis and autophagy within the Beclin 1 interactome"; The EMBO Journal, vol. 29, No. 3; pp. 515-516; Feb. 3, 2010.
Mammucari, C. et al.; "FoxO3 controls autophagy in skeletal muscle in vivo"; Cell Metabolism, vol. 6; pp. 458-471; Dec. 2007.
Mariño, G. et al.; "Self-consumption: the interplay of autophagy and apoptosis"; Nature Reviews Molecular Cell Biology, vol. 15, No. 2; pp. 81-94; Feb. 2014.
Martinez Rodriguez, N.R. et al.; "Expansion of Paneth Cell Populatoin in Response to Enteric *Salmonella enterica* Serovar Typhimurium Infectoin"; Infection and Immunity, vol. 80; pp. 266-275; Jan. 1, 2012.
McCombe, P. A. et al.; "The Role of immune and inflammatory mechanisms in ALS"; Current Molecular Medicine, vol. 11; pp. 246-254; Apr. 1, 2011.
McGoldrick, P. et al.; "Rodent models of amyotrophic lateral sclerosis"; Biochimoca et Biophysica Acta, vol. 1832, Issue 9; pp. 1421-1436; Sep. 2013.
Miller, T.M. et al.; "Gene transfer demonstrates that muscle is not a primary target for non-cell-autonomous toxicity in familial amyotrophic lateral sclerosis" Proceedings of the National Academy of Sciences 103; pp. 19546-19551; Dec. 19, 2006.
Miletta, M.C. et al.; "Butyrate Increases Intracellular Calcium Levels and Enhances Growth Hormone Release from Rat Anterior Pituitary Cells via the G-Protein-Coupled Receptors GPR41 and 43"; Plos One, vol. 9, Issue 10; Oct. 2014.
Mizushima, N. et al.; "In vivo analysis of autophagy in response to nutrient starvation using transgenic mice expressing a fluorescent autophagosome marker"; Molecular Biology of the Cell, vol. 15; pp. 1101-1111; Mar. 2004.
Mizushima, N.; "Autophagy: process and function"; Genes & Development, vol. 21; pp. 2861-2873; Nov. 15, 2007.
Morimoto, N. et al.; "Increased autophagy in transgenic mice with a G93A mutant SOD1 gene"; Brain Research, pp. 112-117; Sep. 2007.
Mukhopadhyay, S. et al.; "Autophagy and apoptosis: where do they meet?"; Apoptosis, vol. 19, No. 4; pp. 555-566; Apr. 1, 2014.
Murrow, L. et al.; "Autophagy as a stress-response and quality-control mechanism: implications for cell injury and human disease"; Annual Review Pathology: Mechanisms of Disease, vol. 8; pp. 105-137; Jan. 24, 2013.
Mshvildadze, M., et al.; "The Infant Intestinal Microbiome: Friend or Foe?"; Early Human Development, vol. 86, Issue 1; 9 pages; Jul. 2010.
Nassif M. et al.; "Targeting autophagy in ALS: a complex mission"; Autophagy, vol. 7, Issue 4; pp. 450-453; Apr. 1, 2011.
Neel, B.A. et al.; "Skeletal muscle autophagy: a new metabolic regulator"; Trends in Endocrinology & Metabolism 24, No. 12; pp. 635-643; Dec. 2013.
Nguyen, Q.T. et al.; "Nerve terminals form but fail to mature when postsynaptic differentiation is blocked: in vivo analysis using mammalian nerve-muscle chimeras"; The Journal of Neuroscience, vol. 20; pp. 6077-6086; Aug. 15, 2000.
National Institute of Neurological Disorders and Stroke: Amyotrophic Lateral Sclerosis (ALS) Fact Sheet; downloaded from the Internet on Mar. 13, 2017 at http://www.ninds.nih.gov/disorders/amyotrophiclateralsclerosis/detail_ALS.htm; 14 pages.
O'Leary, M.F.N. et al.; "Denervation-induced mitochondrial dysfunction and autophagy in skeletal muscle of apoptosis-deficient animals"; American Journal of Physiology—Cell Physiology, vol. 303; pp. 447-454; Aug. 15, 2012.
Onesto, E. et al.; "Muscle cells and motoneurons differentially remove mutant SOD1 causing familial amyotrophic lateral sclerosis"; Journal of Neurochemistry, vol. 118; pp. 266-280; Jul. 1, 2011.
Ouellette, A.J. et al.; "Development of the Gastrointestinal Tract"; Development of Innate Immunitiy in the Small Intestine, vol. 1; pp. 147 and 150; 2000; retrieved from the Internet at https://books.google.com/booksid=YhgKZ_dvda0C&printsec=frontcover&source=gbs_ge_summary_r&cad=0#v=onepage&q&f=false on Jul. 26, 2015.
Pasinelli, P. et al.; "Molecular biology of amyotrophic lateral sclerosis: insights from genetics"; Nature Reviews Neuroscience, vol. 7; pp. 710-723; Sep. 2006.
Pauly, M. et al.; "AMPK activation stimulates autophagy and ameliorates muscular dystrophy in the mdx mouse diaphragm" The American Journal of Pathology, vol. 181; pp. 583-592; Aug. 2012.
Phan, T. G. et al.; "Immune complex relay by subcapsular sinus macrophages and noncognate B cells drives antibody affinity maturation"; Nature Immunology, vol. 10; pp. 786-793; Jul. 2009.
Pizzasegola, C. et al.; "Treatment with lithium carbonate does not improve disease progression in two different strains of SOD1 mutant mice"; Amyotrophic Lateral Sclerosis, vol. 10; pp. 221-228; Jan. 1, 2009.
Pouvreau, S. et al.; "Ca2+ sparks operated by membrane depolarization require isoform 3 ryanodine receptor channels in skeletal muscle"; Proceedings of the National Academy of Sciences 104; pp. 5235-5240; Mar. 20, 2007.
Radu et al.; "Neurovascular Unit in Chronic Pin"; Mediators of Inflammation, vol. 2013; pp. 1-19; Jun. 5, 2013.
Rajapaksa, T. E. et al.; "Claudin 4-targeted protein incorporated into PLGA nanoparticles can mediate M cell targeted delivery"; Journal of Controlled Release, vol. 142; pp. 196-205; Mar. 3, 2010.
Romanello, V. et al.; "Mitochondrial fission and remodelling contributes to muscle atrophy"; The EMBO Journal, vol. 29; pp. 1774-1785; May 19, 2010.
Salzman, N.H. et al.; "Enteric defensins are essential regulators of intestinal microbial ecology"; Natural Immunology, vol. 11, No. 1; pp. 76-83; Jan. 2010.
Sasaki, S.; "Autophagy in spinal cord motor neurons in sporadic amyotrophic lateral sclerosis"; Journal of Neuropathology and Experimental Neurology, vol. 70, No. 5; pp. 349-359; May 1, 2011.
Schoser, B.G. et al.; "Cell death and apoptosis-related proteins in muscle biopsies of sporadic amyotrophic lateral sclerosis and polyneuropathy"; Muscle & Nerve, vol. 24; pp. 1083-1089; Aug. 2001.
Schulz, M. D. et al.; "High-fat-diet-mediated dysbiosis promotes intestinal carcinogenesis independently of obesity"; Nature, vol. 514; pp. 608-512; Oct. 23, 2014.
Shen, L. et al.; "Role of epithelial cells in initiation and propagation of intestinal inflammation. Eliminating the static: tight junction dynamics exposed"; American Journal of Physiology—Gastrointestinal and Liver Physiology, vol. 290; pp. G577-G582; Apr. 1, 2006.
Siu, P.M. et al.; "Mitochondria-associated apoptotic signalling in denervated rat skeletal muscle"; The Journal of Physiology, vol. 565, Issue 1; pp. 309-323; May 1, 2005.
Sun, J. et al.; "Exploring gut microbes in human health and disease: pushing the envelope"; Genes & Diseases, vol. 1; pp. 132-139; Dec. 31, 2014.
Takahashi, N., I. et al.; "IL-17 produced by Paneth cells drives TNF-induced shock"; The Journal of Experimental Medicine, vol. 205; pp. 1755-1761; Aug. 4, 2008.
Tews, D.S. et al.; "DNA-fragmentation and apoptosis-related proteins of muscle cells in motor neuron disorders"; Acta Neurologica Scandinavia, vol. 96; pp. 380-386; Dec. 1, 1997.
Virgin, H. W. et al.; "Autophagy genes in immunity"; Nature Immunology, vol. 10; pp. 461-470; May 2009.
Wang, I.-F. et al.; Autophagy activators rescue and alleviate pathogenesis of a mouse model with proteinopathies of the TAR DNA-

(56) References Cited

OTHER PUBLICATIONS binding protein 43; Proceedings of the National Academy of Sciences; pp. 15024-15029; Sep. 11, 2012.
Wirawan, E. et al.; "Caspase-mediated cleavage of Beclin-1 inactivates Beclin-1-induced autophagy and enhances apoptosis by promoting the release of proapoptotic factors from mitochondria"; Cell Death & Disease, vol. 1: e18; 10 pages; Jan. 1, 2010.
Wong, M. et al.; "Skeletal muscle-restricted expression of human SOD1 causes motor neuron degeneration in transgenic mice"; Human Molecular Genetics, vol. 19; pp. 2284-2302; Jun. 1, 2010.
Wu, S. et al.; "Leaky intestine and impaired microbiome in an amyotrophic lateral sclerosis mouse model"; Physiological Reports, vol. 3, Issue 4; e12356; 10 pages; Apr. 6, 2015.
Xiao, Y. et al.; "Suppressed autophagy flux in skeletal muscle of an amyotrophic lateral sclerosis mouse model upon disease progression"; Physiological Reports, vol. 3, Issue 1; e12271; 12 pages; Jan. 1, 2015.
Xu, Z. et al.; "Molecular and Microscopic Analysis of Bacteria and Viruses in Exhaled Breath Collected Using a Simple Impaction and Condensing Method"; PLoS One, vol. 7; e41137; 8 pages; Jul. 2012.
Yi, J. et al.; "Mitochondrial calcium uptake regulates rapid calcium transients in skeletal muscle during excitation-contraction (E-C) coupling"; Journal of Biological Chemistry, vol. 286; pp. 32436-32443; Sep. 16, 2011.
Yuk, J. M. et al.; "Autophagy and bacterial infectious diseases"; Experimental Molecular Medicine, vol. 44; pp. 99-108; Feb. 29, 2012.
Zhang, X. et al.; "Rapamycin treatment augments motor neuron degeneration in SOD1G93A mouse model of amyotrophic lateral sclerosis"; Autophagy, vol. 7; pp. 412-425; Apr. 1, 2011.
Zhang, X. et al.; "MTOR-independent, autophagic enhancer trehalose prolongs motor neuron survival and ameliorates the autophagic flux defect in a mouse model of amyotrophic lateral sclerosis"; Autophagy, vol. 10; pp. 588-602; Apr. 24, 2014.
Zhou, J. et al.; "Hyperactive intracellular calcium signaling associated with localized mitochondrial defects in skeletal muscle of an animal model of amyotrophic lateral sclerosis"; Journal of Biological Chemistry, vol. 285, No. 1; pp. 705-712; Jan. 1, 2010.
International Search Report dated Aug. 17, 2015 for International Application No. PCT/US2015/030109.

\* cited by examiner

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial
<220> FEATURE:
<223> OTHER INFORMATION: Universal bacteria primer forward

<400> SEQUENCE: 1
tcctacggga ggcagcagt                                                  19

<210> SEQ ID NO 2
<211> LENGTH: 26
<212> TYPE: DNA
<213> ORGANISM: Artificial
<220> FEATURE:
<223> OTHER INFORMATION: Universal bacteria reverse primer

<400> SEQUENCE: 2
ggactaccag ggtatctaat cctgtt                                          26

<210> SEQ ID NO 3
<211> LENGTH: 18
<212> TYPE: DNA
<213> ORGANISM: Artificial
<220> FEATURE:
<223> OTHER INFORMATION: E. Coli forward primer

<400> SEQUENCE: 3
cctacgggag gcagcagt                                                   18

<210> SEQ ID NO 4
<211> LENGTH: 19
<212> TYPE: DNA
<213> ORGANISM: Artificial
<220> FEATURE:
<223> OTHER INFORMATION: E.coli reverse primer

<400> SEQUENCE: 4
cgtttacggc gtggactac                                                  19

<210> SEQ ID NO 5
<211> LENGTH: 19
<212> TYPE: DNA
<213> ORGANISM: Artificial
<220> FEATURE:
<223> OTHER INFORMATION: Bacteroides Fragilis forward primer

<400> SEQUENCE: 5
ggcgcacggg tgagtaaca                                                  19

<210> SEQ ID NO 6
<211> LENGTH: 19
```

```
<212> TYPE: DNA
<213> ORGANISM: Artificial
<220> FEATURE:
<223> OTHER INFORMATION: Bacteroides Fragilis reverse primer

<400> SEQUENCE: 6
caatattcct cactgctgc                                              19

<210> SEQ ID NO 7
<211> LENGTH: 21
<212> TYPE: DNA
<213> ORGANISM: Artificial
<220> FEATURE:
<223> OTHER INFORMATION: Butyrivibrio Fibrisolvens forward primer

<400> SEQUENCE: 7
ctaacacatg caagtcgaac g                                           21

<210> SEQ ID NO 8
<211> LENGTH: 19
<212> TYPE: DNA
<213> ORGANISM: Artificial
<220> FEATURE:
<223> OTHER INFORMATION: Butyrivibrio Fibrisolvens reverse primer

<400> SEQUENCE: 8
ccgtgtctca gtcccaatg                                              19

<210> SEQ ID NO 9
<211> LENGTH: 20
<212> TYPE: DNA
<213> ORGANISM: Artificial
<220> FEATURE:
<223> OTHER INFORMATION: 18S rRNA forward primer

<400> SEQUENCE: 9
aggggagagc gggtaagaga                                             20

<210> SEQ ID NO 10
<211> LENGTH: 20
<212> TYPE: DNA
<213> ORGANISM: Artificial
<220> FEATURE:
<223> OTHER INFORMATION: 18S rRNA reverse primer

<400> SEQUENCE: 10
ggacaggact aggcggaaca                                             20
```

BIOMARKERS FOR RISK ASSESSMENT, DIAGNOSIS AND TARGET MICROBIOME AND INTESTINAL HOMEOSTASIS FOR PREVENTION AND TREATMENT OF AMYOTROPHIC LATERAL SCLEROSIS

RELATED APPLICATIONS

This application claims the benefit under 35 U.S.C. § 371 of International Application No. PCT/US2015/030109, filed May 11, 2015, which claims the benefit of U.S. Provisional Application No. 61/992,007, filed May 12, 2014, which are incorporated by reference herein in their entirety.

FEDERALLY SPONSORED RESEARCH OR DEVELOPMENT

This invention was made with Government support under Grant No. AR057404, awarded by NIAMS/National Institutes of Health. The Government has certain rights in the invention.

BACKGROUND

1. Technical Field Text

Methods of selecting a subject for treatment of amyotrophic lateral sclerosis (ALS) and methods of treatment for subjects having ALS or at risk of developing ALS are provided, and in particular, methods relating to treatment of the gastrointestinal tract and restoration of intestinal beneficial bacteria are provided.

2. Background Information

Amyotrophic lateral sclerosis (ALS) is a fatal neuromuscular disease characterized by progressive motor neuron death and skeletal muscle atrophy. The lifetime risk of ALS is about 1 in 472 (2.1 per 1000) in women and 1 in 350 in men (1). According to ALS Association website (5), the prevalence of ALS is between 6-8 cases per 100,000 population, and nearly 22,600 Americans are living with ALS at any one time. Since ALS is a disease of aging, as the U.S. population increases and ages, an increase in the prevalence of ALS can be anticipated. 95% of patients die from respiratory failure, usually within 3-5 years after the onset of symptoms. Despite intensive research on the pathogenesis of ALS, there are no cures for ALS. Riluzole, the only FDA approved treatment, extends patient life span for only a few months, but does not relieve symptoms (3).

About 10 percent of all ALS cases are inherited, while the vast majority ALS cases are sporadic (SALS) that occurs apparently at random with no clearly identified risk factors. There is no one test providing a definitive diagnosis of ALS. Instead, the diagnosis of ALS is primarily based on the symptoms and signs the physician observes in the patient and a series of tests to rule out other diseases (4). Thus, there is an urgent need to identify the potential ALS patients and prevent the motor neuron damage at early stages.

Both SALS and FALS manifest similar pathological and clinical phenotypes, suggesting that different initiating molecular insults promote a similar neurodegenerative process. Many cases of FALS (20-25%) are associated with mutations in the Cu/Znsuperoxide dismutase gene (SOD1). Transgenic mice (G93) harboring human ALS-causing SOD1 mutations recapitulate the neuronal and muscle impairment of human ALS patients and thus these mice are expensively used to investigate the pathomechanisms of ALS and trial new therapeutics (2,3).

The microbiome community modulates numerous aspects of human physiology and is a critical factor in the development of chronic diseases (6). Intestinal epithelial cells are consistently exposed to bacteria, a process which plays a key role in development, renewal, and immunity (7-9). Frequent microbial challenges to epithelial cells trigger discrete signaling pathways, promoting molecular changes, such as the secretion of cytokines and chemokines, and alterations to molecules displayed at the epithelial cell surface. However, there is no study exploring the intestinal microbiome and epithelial functions in ALS.

What is needed are biomarkers for ALS diagnosis and risk assessment. There is also a need for a treatment for ALS patients.

BRIEF SUMMARY

Methods of selecting a subject for treatment of amyotrophic lateral sclerosis (ALS) and methods of treatment for subjects having ALS or at risk of developing ALS are provided. The method of selecting subjects for treatment includes obtaining a biological sample from the subject, where the sample is obtained from the subject's gastrointestinal tract (feces and mucosa) or skeletal muscle. The method further includes measuring a biomarker in the subject's sample and selecting the subject for treatment of ALS when the biomarker measurement in the subject's sample is lower or higher relative to a control measurement.

DETAILED DESCRIPTION

Figure 1:
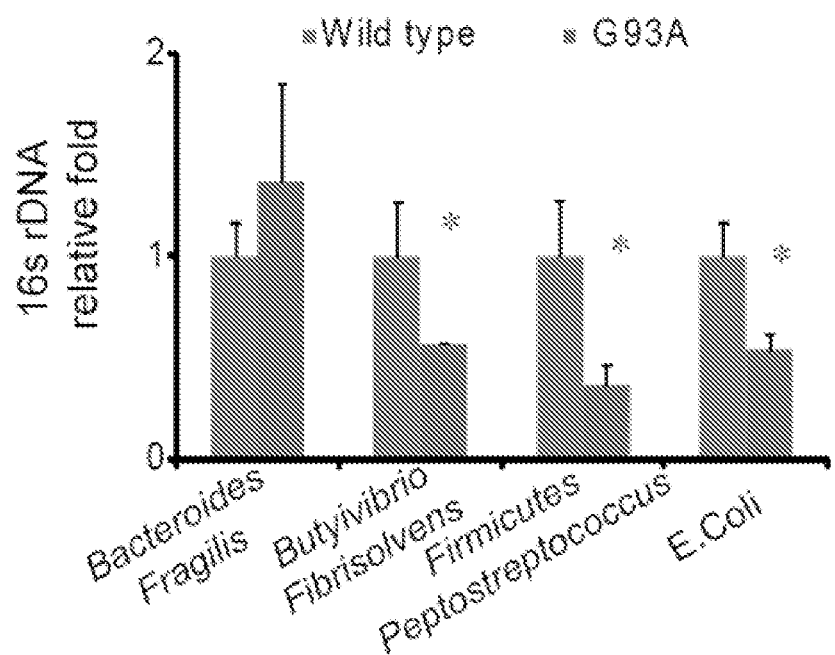
FIG. 1 illustrates that *Butyrivibrio fibrisolvens* in fecal samples is decreased in G93A amyotrophic lateral sclerosis model mice (3 month old, with symptom). Real-time PCR of bacterial universal 16srDNA and 16s rDNA for *E. coli*, Bacteroides fragilis and *Butyrivibrio fibrisolvens* in fecal from derived from both 3-month old G93A and wild type mice. Primers specific to universal 16srDNA were used as an endogenous control to normalize loading between samples. The relative amount of 16S rRNA in each sample was estimated using the $\Delta\Delta CT$ method. (n=3, *:P<0.05)

The embodiments disclosed below are not intended to be exhaustive or to limit the scope of the disclosure to the precise form in the following description. Rather, the embodiments are chosen and described as examples so that others skilled in the art may utilize its teachings.

Methods of selecting a subject for treatment of amyotrophic lateral sclerosis (ALS) and methods of treatment for subjects having ALS or at risk of developing ALS are provided.

In some embodiments, a biological sample is obtained from a subject and a biomarker in the sample is measured relative to a control sample. The biological sample may be obtained from any source from the subject and in particular, the sample may be obtained from the gastrointestinal tract or from skeletal muscle. In some embodiments, the subject's sample is a fecal sample.

In some embodiments, a microbial profile may be measured in the sample from the subject. The microbial profile may include, but is not limited to the following *Butyivibrio fibrosolvens, Firmicutes peptostreptococcus, Escherichia coli*, bacteriodes and butyrate-producing bacteria.

In some embodiments, a microbial marker may be measured in the sample from the subject. Microbial markers may include, but are not limited to butyryl-coenzyme A CoA transferase or anti-microbial peptides (AMPs),including defensins. These markers may be used in combination inflammatory markers, such as IL-17, and permeability changes, such as decreased ZO-1.

Treatment Stratification

In some embodiments, the analysis of the biomarker panel may be used to determine a treatment regime for the subject. In some embodiments, the measurement of one or more biomarkers may be used to determine whether to follow up at a later time point with the subject to repeat the measurement of the one or more biomarkers; to provide additional testing; to begin a treatment, to continue the same treatment or to modify the treatment regime for a subject. The treatment may be started or modified by administering a drug or changing the drug administered to the subject or to add an additional drug to an existing drug treatment regime, to change the dosage or other changes.

"Treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to ALS or a halting in the progression of a disease such as ALS.

In some embodiments, treatment may include administering one or more of a microbial supplement, probiotics, prebiotics, a bacterial product (such as short chain fatty acid), or a pharmaceutical or b) applying a therapeutic regimen for treating ALS.

In some embodiments, the treatment may include an oral administration of a butyrate compound. The butyrate compound may be sodium butyrate calcium butyrate, tributyrin, or other derived butyrate but is not limited thereto. Other butyrate compounds known in the art may also be used. In some embodiments, the dose of the butyrate compound administered to the subject may be in the range from about 500 mg to 2000 mg per day for patients. In some embodiments, the dose of the butyrate compound to be administered alone or in combination therapy warm-blooded animals, for example humans, is preferably from approximately 0.01 mg/kg to approximately 1000 mg/kg, more preferably from approximately 1 mg/kg to approximately 100 mg/kg, per day, divided preferably into 1 to 3 single doses which may, for example, be of the same size. Usually children receive half of the adult dose, and thus the preferential dose range for the inhibitor in children is 0.5 mg/kg to approximately 500 mg/kg, per day, divided preferably into 1 to 3 single doses that may be of the same size.

A compound can be administered alone or in combination with another autophagy activators, possible combination therapy taking the form of fixed combinations or the administration of a compound and another inhibitor being staggered or given independently of one another. Long-term therapy is equally possible as is adjuvant therapy in the context of other treatment strategies, as described above. Other possible treatments are therapy to maintain the subject's status after symptom amelioration, or even preventive therapy, for example in subjects at risk.

Effective amounts of the compounds described herein generally include any amount sufficient to detectably ameliorate one or more symptoms of ALS, or by detecting an inhibition or alleviation of symptoms of ALS. The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

According to the methods of treatment of the present invention, ALS is reduced or prevented in a subject such as a human or lower mammal by administering to the subject an amount of an agent, in such amounts and for such time as is necessary to achieve the desired result. An "amount that is effective to modifies a microbiome profile of the gastrointestinal tract of the subject relative to a control subject" of a compound or an inhibitor refers to a sufficient amount of the agent, at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

Compositions for administration of the active agent in the method of the invention may be prepared by means known in the art for the preparation of compositions (such as in the art of veterinary and pharmaceutical compositions) including blending, grinding, homogenising, suspending, dissolving, emulsifying, dispersing and where appropriate, mixing of the active agent, together with selected excipients, diluents, carriers and adjuvants.

For oral administration, the composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methyl cellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further include one or more emulsifying agents. Suitable emulsifying agents include dispersing agents as exemplified above or natural gums such as guar gum, gum acacia or gum tragacanth.

EXAMPLE 1

Gastrointestinal Biomarkers

Real-Time PCR Measurement of Bacterial DNA

DNA was extracted from colonic tissues. 16S rDNA PCR reactions were performed with the following primers: Universal bacteria (10) (forward: 5'-TCCTACGG-GAGGCAGCAGT-3'(SEQ ID NO: 1); reward:5'-GGAC-TACCAGGGTATCTAATCCTGTT-3' (SEQ ID NO: 2)), *E. coli* (forward: 5'-CCTACGGGAGGCAGCAGT-3' (SEQ ID NO: 3); reward:5'-CGTTTACGGCGTGGACTAC-3' (SEQ ID NO: 4)), Bacteroides fragilis (forward: 5'-GGCGCACGGGTGAGTAACA-3' (SEQ ID NO: 5); reward:5'-CAATATTCCTCACTGCTGC-3' (SEQ ID NO: 6)) and *Butyrivibrio fibrisolvens* (forward: 5'-CTAACA-CATGCAAGTCGAACG-3' (SEQ ID NO: 7); reward:5'-CCGTGTCTCAGTCCCAATG-3' (SEQ ID NO: 8)), Primers specific to 18S rRNA$^{74}$ (forward: 5'-AGGGGAGAGCGGGTAAGAGA-3' (SEQ ID NO: 9); reward:5'-GGACAGGACTAGGCGGAACA-3' (SEQ ID NO: 10)) were used as an endogenous control to normalize loading between samples. The relative amount of 16S rDNA in each sample was estimated using the $\Delta\Delta CT$. Results are shown in FIG. 1.

Figure 2:
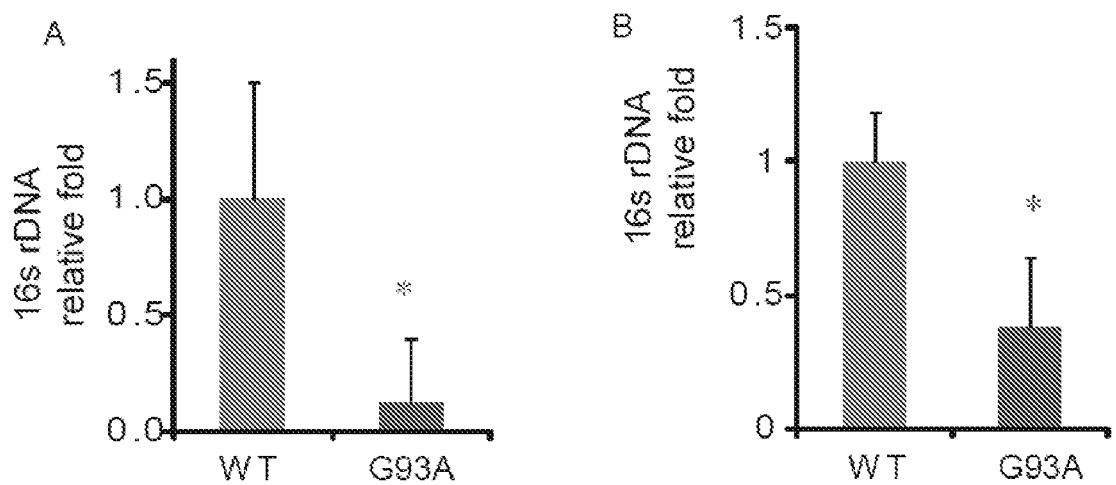
FIG. 2A-2B illustrates that the Butyryl-coenzyme A CoA transferase gene expression is decreased in G93A amyotrophic lateral sclerosis model mice. A: 2 month mice, without symptom; B: 3 month old mice, with symptoms. Real-time PCR of Butyryl-coenzyme A CoA transferase genes in fecal from both G93A and wildtype mice. Primers specific to bacterial 18S rRNA were used as an endogenous control to normalize loading between samples. The relative amount in each sample was estimated using the $\Delta\Delta CT$ method. (WT: wild type control mice; n=3, *:P<0.05)

Real Time quantitative PCR of Butyryl-coenzyme A CoA transferase genes in fecal samples from both G93A and wildtype mice Total RNA was extracted from fecal samples using TRIzol reagent (Life technologies, 15596-02). RNA was first reverse-transcribed into cDNA with the iScript cDNA synthesis kit (Bio-Rad, 170-8891) according to the manufacturer's manual. The RT-cDNA reaction products were subjected to quantitative real-time PCR using CTFX 96 Real-time system (Bio-Rad, C1000) and SYBR green supermix (Bio-Rad, 172-5124) according to the manufacturer's directions. All expression levels were normalized to β-actin levels of the same sample. Percent expression was calculated as the ratio of the normalized value of each sample to that of the corresponding untreated control cells. All real-time PCR reactions were performed in triplicate. Primers specific to bacterial 18S rRNA were used as an endogenous control to normalize loading between samples. The relative amount in each sample was estimated using the $\Delta\Delta CT$ method. Results are shown in FIG. 2.

Tight Junction Comparison Associated with Intestinal Permeability

Proximal colon epithelial cells were freshly isolated and paraffin-embedded after fixation with 10% neutral buffered formalin. Immunofluorescence was performed on paraffin-embedded sections (5 µm). After preparation of the slides as described previously (11), tissue samples were incubated with anti-ZO-1 (Santa Cruz) at 4° C. overnight. Samples were then incubated with sheep anti-goat Alexa Fluor 594 (Life technologies, A11058) and DAPI (Life technologies, D1306) for 1 hour at room temperature. Tissues were mounted with SlowFade (Life technologies, s2828), followed by a coverslip, and the edges were sealed to prevent drying. Specimens were examined with Zeiss laser scanning microscope (LSM) 710. The tight junction protein ZO-1 shows discontinuity in proximal colon epithelial cells in G93A amyotrophic lateral sclerosis (ALS) model mice (3 month, with symptom). Immunostaining was performed in mouse colon from both 3-month old G93A and wild type mice.

Paneth Cell Measurements

Paneth Cell Counting.

Figure 3:
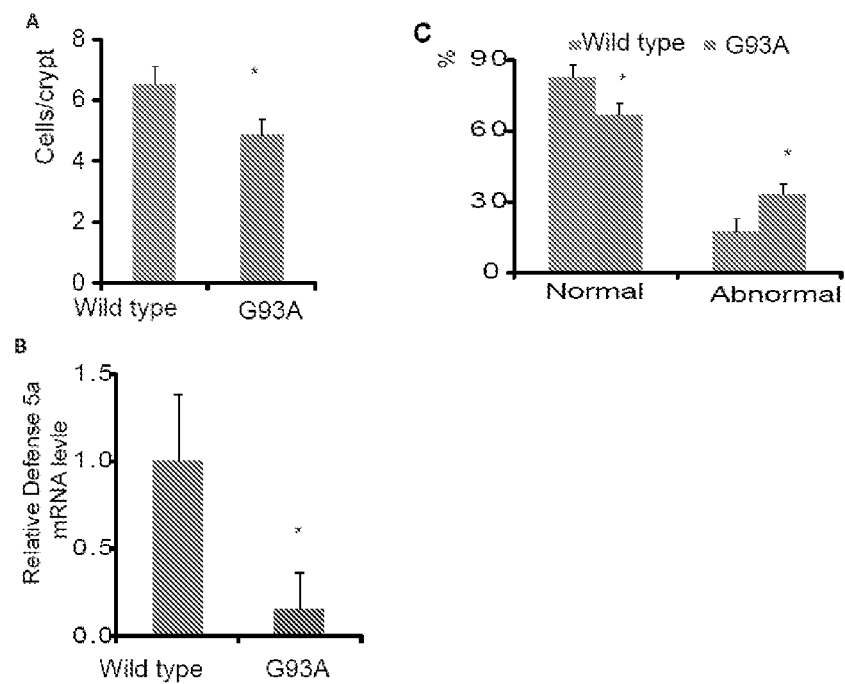
FIG. 3A-3C illustrates defects in Paneth cells in intestine of ALS mice. A. Number of Paneth cell/crypt. B. Defense 5 alpha mRNA level. In 3 month old mice with symptoms. C. Percentage of normal and abnormal Paneth cells.
Figure 4:
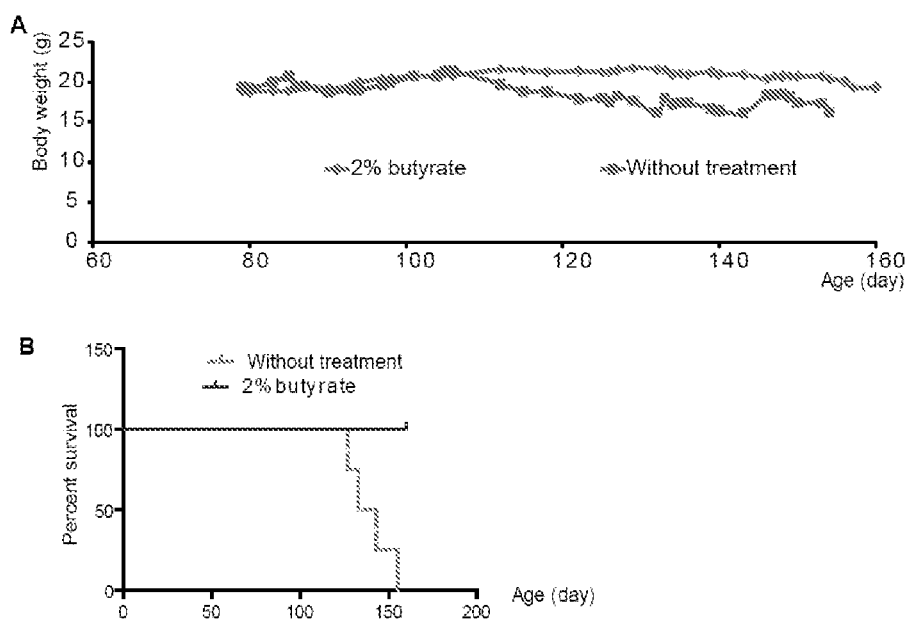
FIG. 4A-4B illustrates that oral administration of sodium butyrate prevents body weight loss (A) and extends survival time in G93A amyotrophic lateral sclerosis model mice. Nine G93A mice were divided into a treatment group (n=4) and a butyrate group (n=5). Butyrate mice started to drink 2% sodium butyrate in the drinking water bottle from age 63 days, without treatment mice drank regular water mice. Without treatment mice died on day 127, 133, 143, 155 separately. All the butyrate mice survived at least one additional month or longer.

Paneth cells in mouse ileal cells were counted after anti-lysozyme immunofluorescence staining. The patterns of lysozyme expression in Paneth cells were classified into four categories: normal (D0), disordered (D1), depleted (D2) and diffuse (D3) according to published methods. (12) Results are shown in FIGS. 3A and 3C.

Real Time Quantitative PCR of Defensins

Total RNA was extracted from mouse ileal epithelial cells using TRIzol reagent (Life technologies, 15596-02). RNA was first reverse-transcribed into cDNA with the iScript cDNA synthesis kit (Bio-Rad, 170-8891) according to the manufacturer's manual. The RT-cDNA reaction products were subjected to quantitative real-time PCR using CTFX 96 Real-time system (Bio-Rad, C1000) and SYBR green supermix (Bio-Rad, 172-5124) according to the manufacturer's directions. All expression levels were normalized to β-actin levels of the same sample. Percent expression was calculated as the ratio of the normalized value of each sample to that of the corresponding untreated control cells. All real-time PCR reactions were performed in triplicate. Optimal primer sequences were designed using Primer-BLAST (see NCBI blast at nih.gov) or were obtained from Primer Bank (see primer bank at harvard.edu) primer pairs. Results are shown in FIG. 3B.

Butyrate Treated Mice Model

Mice were divided into control and butyrate group. Butyrate group mice were given 2% sodium butyrate (Sigma, St. Louis, Mo.) water ad libitum from age 63 days. The untreated control group was maintained on tap water throughout the experiment. Without treatment mice died on day 127, 133, 143, 155 separately. All the butyrate mice survived.

Western Blot Analysis and Antibodies

Mouse intestinal mucosal cells were collected by scraping from mouse colon, including proximal and distal colon, as previously described (Liao et al. 2008; Wu et al. 2014). Briefly, mouse mucosal cells were lysed in lysis buffer (1% Triton X-100 (9100; Sigma-Aldrich, St. Louis, Mo.), 150 mmol/L NaCl (J. T. Baker 3624-19), 10 mmol/L Tris (Fisher Scientific, Waltham, Mass., BP152-5) pH 7.4, 1 mmol/L EDTA (Fisher Scientific, BP120-1), 1 mmol/L EGTA (Sigma-Aldrich, E3889) pH 8.0, 0.2 mmol/L sodium orthovanadate (Sigma-Aldrich, S6508) and protease inhibitor cocktail (Roche Diagnostics, Nutley, N.J., 118367001). Cultured cells were rinsed twice in ice-cold Hanks' balanced salt solution (Sigma-Aldrich, H1387), lysed in protein loading buffer (50 mmol/L Tris, pH 6.8, 100 mmol/L dithiothreitol [Amresco, Solon, Ohio, 0281], 2% SDS [Sigma-Aldrich, L3771], 0.1% bromophenol blue [IBI Scientific, Peosta, Iowa, 1674040], and 10% glycerol [Sigma-Aldrich, G5516]) and sonicated (Branson Sonifier, Danbury, Conn. 250). An equal amount of protein was separated by SDS-polyacrylamide gel electrophoresis, transferred to nitrocellulose (Bio-Rad, Hercules, Calif., 162-0112), and immunoblotted with primary antibodies: Occludin (Zymed, Las Condes, Santiago, Chile, 33-1500), ZO-1 (Life Technologies, Carlsbad, Calif., 33-9100), E-cadherin (BD, Franklin Lakes, N.J., 610405), or b-actin (Sigma-Aldrich, A1978) antibodies and visualized by ECL chemiluminescence (Thermo Scientific, Waltham, Mass., 32106). Membranes probed with more than one antibody were stripped before reprobing. Western blot bands were quantified using Image Lab 4.01 (Bio-Rad).

Il-17 ELISA

Mouse blood samples were collected by cardiac puncture and placed in tubes containing EDTA (10 mg/mL; Liao et al.

2008). Mouse intestinal mucosal cells were collected by scraping from mouse small intestine and were lysed in lysis buffer, equal amount of protein was used to detect cytokines. Cytokines were measured using a mouse cytokine 20-Plex Panel kit (Life Technologies, LMC0006) according to the manufacturer's instructions. The cytokines included IL-17. Cytokines were analyzed with the Luminex detection system (PerkinElmer CS1000 Autoplex Analyzer).

Fecal Microbiome 454 Pyrosequencing

Fecal microbiome sequencing was done as previously described (Wu et al. 2014). In short, prepared the tubes for microbial sampling with autoclave and then irradiated with ultraviolet light. Collected fecal and placed into the specially prepared tubes. The samples were kept at low temperature with dry ice and mailed to Research and Testing Laboratory, Lubbock, Tex., for 454 pyrosequencing. Principal coordinates analysis (PCoA) of unweighted UniFrac distances was plotted using quantitative insights into microbial ecology (QIIME). To determine differences in microbiota composition among the animal groups, the analysis of similarities (ANOSIM) function in the statistical software package PRIMER 6 (PRIMER-E Ltd., Lutton, UK) was used on the unweighted UniFrac distance.

Statistical Analysis. Data are expressed as mean±SD. Differences between two samples were analyzed by Student's t test. Differences among three or more groups were analyzed using ANOVA with GraphPad Prism 5. P-values of 0.05 or less were considered statistically significant.

Disrupted Junction Structure in the Intestine of G93A Mice

Figure 9:
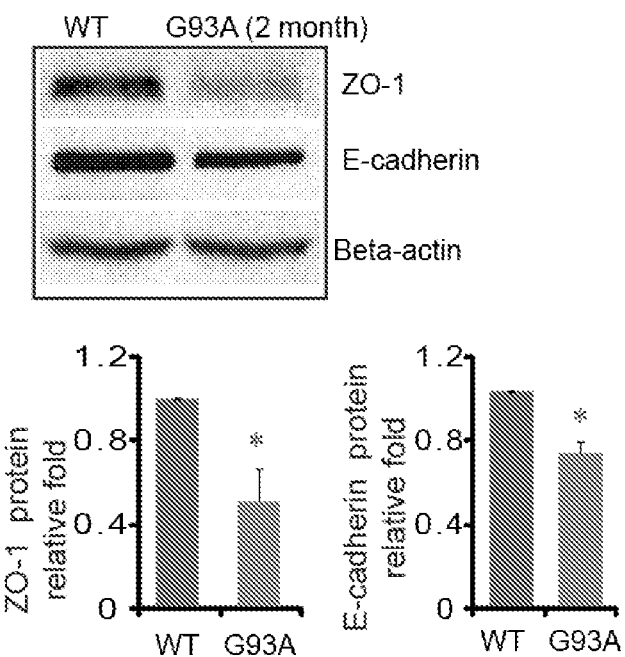
FIG. 9 illustrates Western blots of ZO-1 and E-cadherin in the colon. The relative band intensities of ZO-1 and E-cadherin are presented as means±SD (n=3 per group, *P<0.05)

G93A mice are asymptomatic until after 3 months of age (Gurney et al. 1994). To test whether the GI abnormality occurs before ALS symptom onset, we used 2-month-old G93A mice. An important component of the intestinal structure is the intercellular junction between the epithelial cells, namely tight junctions (TJs) and adherens junctions (AJs). An AJ is a cell junction in which the cytoplasmic face is linked to the actin cytoskeleton. Internal epithelial cells often rely on TJs and AJs to seal the paracellular space and regulate the permeability of the mucosal barrier. Using Western blot analysis, we found that ZO-1 protein expression was significantly decreased in the G93A gut compared to the WT mice (FIG. 9). The AJ protein E-cadherin in the intestine was also reduced in the G93A mice compared to the WT mice (FIG. 9). Our immunostaining data further showed an abnormal distribution of the TJ protein ZO-1 in the membrane of intestinal epithelial cells in ALS mice at the age of 2 months (not shown). In contrast, ZO-1 was restricted to cellular borders and distributed in a smooth and organized pattern at the apical side of colon the wild-type (WT) mice. Weaker staining of E-cadherin was found in the G93A mice than in the WT mice, which was consistent with the reduced E-cadherin expression at the protein level in the G93A mice. Although there was less E-cadherin in the G93A mice, it was still evenly distributed in colon. We observed the H&E staining of the intestine of G93A mice at 2 months of age before the onset of disease. Interestingly, significant pathological changes in the colon of G93A mice were not found. We studied the expression and distribution of ZO-1 and E-cadherin in colon because colon harbors the most abundant microflora and allows us to study the host-bacteria interactions. We did not find obvious pathological changes in the small intestine of G93A mice by H&E (data not shown). Taken together, these data showed a significant reduction in the ZO-1 and Ecadherin proteins in the ALS model, and those changes could occur before the onset of ALS neuromuscular symptoms.

G93A Mice had Increased Inflammatory Cytokines and Intestinal Permeability

Figures 11A, 11B, 11C:
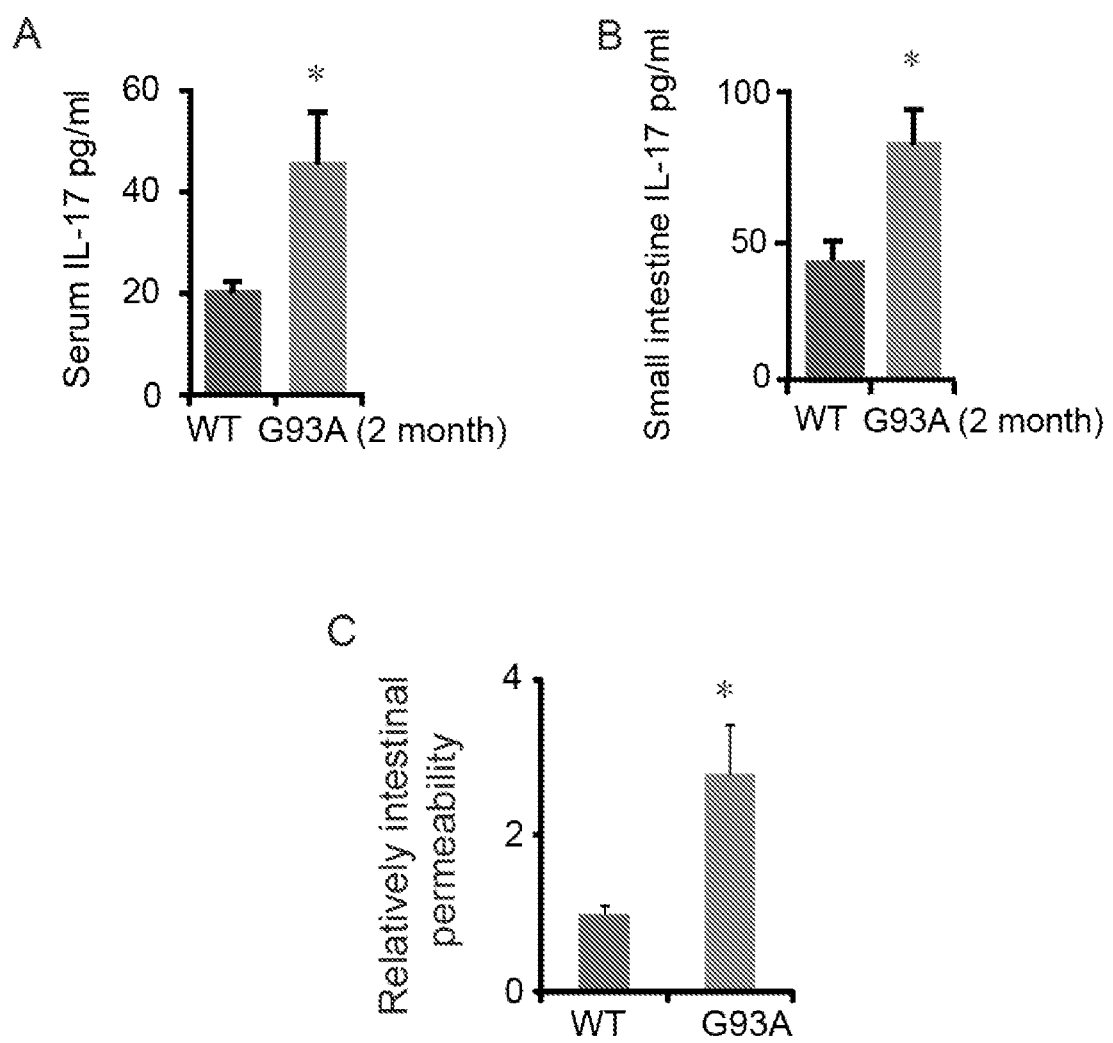
FIG. 11A-11C illustrates enhanced IL-17 and intestinal permeability in amyotrophic lateral sclerosis (ALS) mice. (A,B) The inflammatory cytokine IL-17 in mouse serum and the small intestine (n=3, *P<0.05). (C) Intestinal permeability is increased in ALS mice (n=3, *P<0.05).

The TJ structure plays a critical role in the intestinal barrier and inflammation (Farhadi et al. 2003; Shen and Turner 2006; Blikslager et al. 2007; Laukoetter et al. 2007; Ling et al. 2008; Rajapaksa et al. 2010). Blood and small intestinal tissues were collected to measure the inflammatory cytokine IL-17 by ELISA. As shown in FIG. 11A, significantly increased serum IL-17 levels in the young G93A mice (2-month-old) were observed. Moreover, IL-17 was enhanced in the intestine in G93A mice (FIG. 11B). These data indicate a preinflammatory state in the ALS mice before the onset of disease. Immunofluorescence-tagged FITC-dextran was also administered by gavage to each mouse for the permeability assay (FIG. 11C). Mouse serum was collected to measure the intensity of fluorescence. Higher FITC readings indicated higher permeability of the intestine. We observed a twofold increase in the fluorescence reading in G93A mouse serum compared to WT mouse serum. Overall, the in vivo data demonstrate significantly increased inflammatory cytokine IL-17 levels and altered intestinal integrity (leaky gut) in ALS mice.

Abnormal Paneth Cells in G93A Mice

Figure 10:
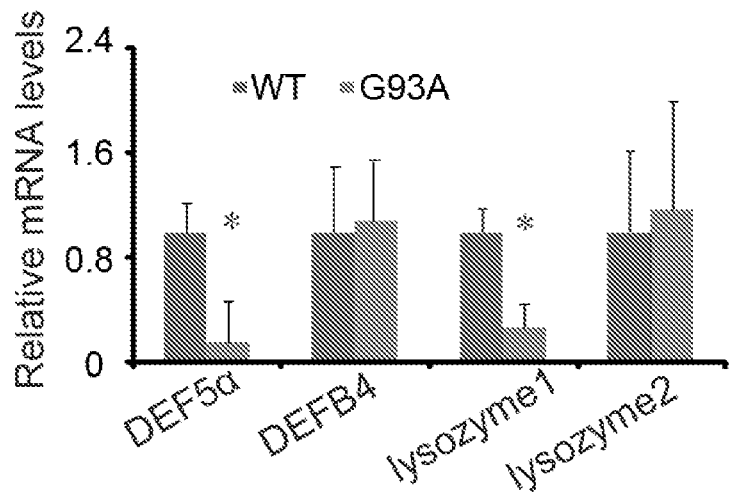
FIG. 10 illustrates Defendin 5 alpha mRNA level in 3-month-old mice with symptoms (n=3, *P<0.05).

Paneth cells are specialized epithelial cells in the small intestine that regulate autophagy activity and host-bacterial interactions in the gut (Schulz et al. 2014; Wu et al. 2014). Lysozymes are components and markers of the Paneth cell secretory granule. Abnormal Paneth cells show disorganized or diminished granules that exhibit diffuse cytoplasmic lysozyme staining (Cadwell et al. 2008). We specifically noticed the decreased number of normal Paneth cells shown as the number of Paneth cells per crypt (FIG. 3A) in G93A mice. The percentage of abnormal Paneth cells was significantly increased in G93A mice (FIG. 3C). The granules of Paneth cells contain antimicrobial peptides (AMPs). A decreased amount of the AMP defensin 5 alpha was also found in the G93A intestine of 3-month-old mice with symptoms (FIG. 10). In contrast, the other AMPs, such as defensin 4 beta, were not changed in the G93A intestine. Paneth cells are associated with autophagic activity in the intestine. Furthermore, a significant reduction in lysozyme 1 in the G93A intestine was found, although lysozyme two was not changed. These data indicate a potential dysfunction of Paneth cells and autophagy in the intestine of G93A mice.

Abnormal Intestinal Microbiome in G93A Mice

Figure 12A:
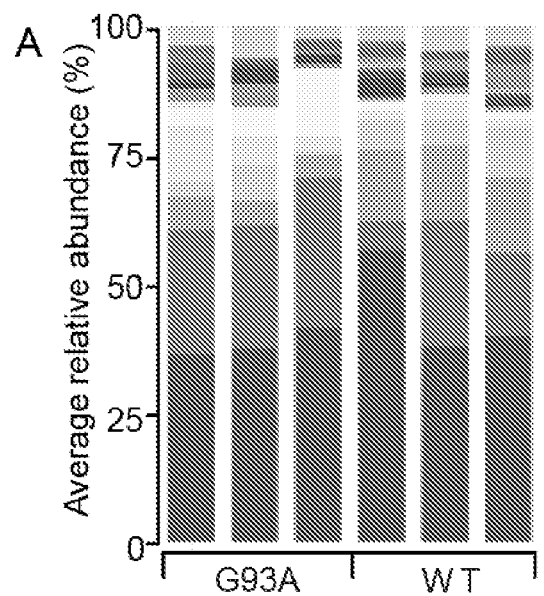
FIG. 12A-12B illustrates the shift of fecal microbial communities in ALS mice. (A) Bacterial community of fecal samples from ALS and WT mice using 454 16srRNA sequencing data (n=3 per group). (B) Principal coordinates analysis (PCoA) of unweighted UniFrac distances of 16S rRNA genes showing that fecal microbial communities differ in ALS and WT mice.
Figure 12B:
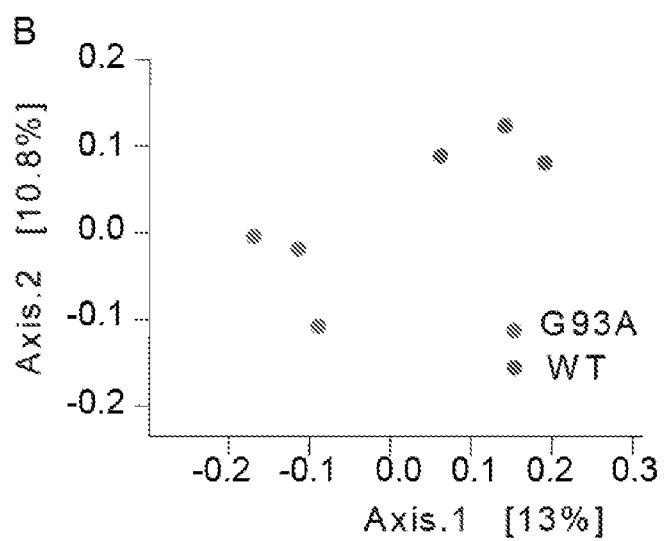

The Paneth cells produce IL-17 (Takahashi et al. 2008), sense microbes and secrete AMPs. Although Paneth cells are located in the ileum, AMPs are released to the entire intestine. Enteric AMPs are essential regulators of intestinal microbial ecology (Salzman et al. 2009). Furthermore, we collected fecal samples from G93A mice and tested the bacterial profile by 16rRNA analysis. Our PCR data showed an abnormal intestinal microbiome, in which butyrate-producing bacteria (*Butyrivibrio fibrisolvens*), *E. coli*, and *Fermicus*, were reduced (FIG. 1). This change occurs in young ALS mice at the age of 2 months, which is before disease onset. We further collected fecal samples from G93A mice and tested the bacterial profile by 454 16rRNA sequencing. The relative abundance of bacteria was shifted in G93A mice compared to WT mice (FIG. 12A). Principal coordinate analysis (PCoA) indicated that fecal microbial communities differ in G93A mice compared to WT mice (FIG. 12B). Overall, our data showed a shift in the intestinal microbiome profile in G93A mice.

Discussion

In the current study, for the first time, it has been demonstrated that the gut of an ALS mouse model (G93A) loses its integrity, is unable to maintain its structure and function, and the microbiome profile at the early stage of disease progression is altered. A damaged TJ structure was discovered with increased gut permeability and higher levels of the inflammatory cytokine IL-17. The expression levels of the junction proteins ZO-1 and E-cadherin were significantly reduced in the intestine of G93A mice, which may explain the increased permeability and leakage in the intestine. Furthermore, a significantly increased number of abnormal Paneth cells in G93A mice was found. In accordance with the key roles of Paneth cells in regulating innate immune responses and shaping the gut microbiome, a reduced protein level of the AMP defensin 5 alpha and a shifted profile of the intestinal microbiome were also demonstrated in the intestine of G93A mice. The structural and physiological changes mirror the population shift in the intestinal microbiome (dysbiosis) of G93A mice.

The early changes of the intestinal microbiome and the leaky gut likely promote a systematic inflammatory response. Indeed, inflammation in ALS has been reported in human (McCombe and Henderson 2011). Our data regarding enhanced IL-17 in the blood are in line with the report. Moreover, the increased IL-17 level in the G93A intestine provides new evidence of a link between intestinal inflammation and ALS.

Autophagy is a key process that responds to injury and pathogens in host defense systems (Yuk et al. 2012; Murrow and Debnath 2013) and eliminates misfolded proteins (Klionsky et al. 2008). Dysregulation of autophagy is implicated in ALS (Li et al. 2008; Sasaki 2011; Crippa et al. 2013). A reduced autophagy flux has been reported in G93A motor neurons (Zhang et al. 2014). Our recent study demonstrated a suppressed autophagic response in the skeletal muscle of young G93A mice before disease onset (Xiao et al. 2015). In the intestine, we specifically noticed a decrease in normal Paneth cells and a reduction in lysozyme 1, one of the proteases in lysosomes associated with autophagy maturation (Phan et al. 2009; Virgin and Levine 2009). Decreased levels of the antimicrobial peptide defensin were also found in the G93A intestine. Our data indicate a potential dysfunction of autophagy in the intestine of G93A mice, which may lead to a reduced capacity to eliminate misfolded proteins and promote gut dysfunction in G93A mice. Protein aggregation of SOD1-mutant protein is a hallmark of ALS pathology (Deng et al. 2006; Ivanova et al. 2014; Kim et al. 2014). The ALS-causing mutation $SOD1^{G93A}$ forms protein aggregates in motor neurons (Deng et al. 2006). Our previous study shows that $SOD1^{G93A}$ forms protein aggregates in skeletal muscle fibers, which lead to mitochondrial dysfunction (Luo et al. 2013). SOD1 gene mutations may also form protein aggregates in the intestine of G93A mice. It has been reported that mice overexpressing the antioxidant enzyme SOD1 have significantly reduced intestinal tissue damage (Lee et al. 2014). Thus, we speculate that $SOD1^{G93A}$ mutations may play an essential role in pathophysiological functions in the intestine. It is possible that G93A mice may develop an age- or stress-dependent phenotype within the GI system. This will be examined in our future study by the evaluation of G93A mice at different stages of development. Understanding the pathogenic mechanism will help to identify new targets for improving therapeutic strategies for ALS. The gut microbiome plays essential roles in neurological diseases, such as autism and Parkinson's disease (Collins and Bercik 2009; Finegold et al. 2010; Hsiao et al. 2013). A leaky gut with an increased translocation of LPS from gram-negative enterobacteria also plays a role in the inflammatory pathophysiology of depression (Maes et al. 2008). Our data provide evidence regarding dysbiosis, a shift of bacterial populations, in an ALS mouse model. Gut microbial interactions are complex, fluid, and capable of adjusting to physiological perturbations that are encountered on a daily basis. However, selective shifts in the gut microbiota as a consequence of host pathobiology can upset critical intermicrobe as well as host-microbe relationships and initiate pathophysiological processes leading to disease. Two examples of this include the loss of beneficial microbes and their products and the emergence of disease-promoting microbes that produce microbial metabolites and proinflammatory mediators, which negatively impact the intestine and other organ systems (Sun and Chang 2014). We observed a reduction in butyrate-producing bacteria (*Butyrivibrio fibrisolvens*). These changes occur in young G93A mice before ALS onset. A leaky gut could contribute to the altered microbiome environment that leads to reduced beneficial bacterial products, such as short-chain fatty acids (SCFAs), or enhanced toxic bacterial products, such as LPS. Butyrate is an SCFA that modulates the physiology of the host through binding of G protein-coupled receptors (GPCR; Fung et al. 2012; Miletta et al. 2014). However, to our knowledge, there is no report of bacterial products and their receptors that play a role in neuromuscular degeneration in ALS progression or functional changes in other organs. Our current study indicates that impaired gut-neuromuscular crosstalk may actively contribute to ALS progression.

In summary, our current study has identified changes in the gut microbial profile and the level of the inflammatory cytokine IL-17 as well as an abnormal intestinal junction structure and function (permeability and Paneth cells) in an ALS mouse model. Our studies have provided the first insight into the potential contribution of aberrant intestinal homeostasis in ALS progression. ALS patients often come to the clinic only after their disease has become symptomatic, making it difficult to understand the early events leading to the disease. The G93A mouse model allows us to examine the roles of genetic factors and other organs in the early events of disease development and to elucidate the potential pathogenic mechanisms.

EXAMPLE 2

Skeletal Muscle Biomarkers

Characterization of the autophagosome formation and the intracellular targeting of LC3 in live skeletal muscle fibers.—The microtubule-associated protein light chain 3 (LC3) is one of the major protein markers of autophagosome in eukaryotes (45). The LC3 fused to fluorescent proteins (LC3-GFP or LC3-RFP) were successfully used to monitor autophagosome formation in various tissues types including skeletal muscle (41, 46). In the current study, LC3-RFP was overexpressed to examine autophagosome formation in live skeletal muscle. The expression pattern of LC3-RFP protein in skeletal muscle was first characterized under the experimental conditions. The LC3-RFP plasmid was transfected into the FDB muscle of a live mouse. Seven days post-transfection, the transfected FDB muscle was enzyme-digested to isolate individual muscle fibers for confocal imaging studies. Unlike reported for other cells, the cytosol expression of LC3-RFP in skeletal muscle fibers is not homogeneous, instead it forms transversal parallel rolls inside the muscle fiber. The isolated live muscle fibers were also incubated with MitoTracker DeepRed (MitoTracker) to visualize mitochondria. It is known that mitochondria form double rolls alone the Z-line in FDB muscle (43, 47). The profile derived from the overlay image of LC3-RFP and MitoTracker suggests that LC3-RFP is distributed evenly along the Z-disc between the double rolls of mitochondria. The evenly distributed fluorescent rolls of LC3-RFP are not considered as the autophagosome formation. The autophagosome formation is only identified as the fluorescent vesicles formed outside the Z-line. The ratio of the area-sum of the fluorescent vesicles over the area of the imaged fiber segment was applied to quantify the autophagosome formation in skeletal muscle fibers. Autophagy is a tightly regulated cellular process that targets autophagosomes for lysosomal degradation. To confirm if the observed LC3-RFP fluorescent vesicles are autophagosomes, the muscle fibers expressing LC-RFP with lysosome marker were examined simultaneously. The isolated live FDB muscle fibers expressing LC3-RFP were incubated with LysoTrack Green to visualize lysosome vesicles. LC3-RFP and LysoTracker Green were then excited at 543 nm and 488 nm respectively. Interleaved excitation and spectrally separated emission wavelengths permitted simultaneous recording of the LC3-RFP and LysoTracker Green signals. Lysosomes were observed as green fluorescent vesicles. The results of the overlay image of LC3-RFP and LysoTracker Green show that the LC3-RFP fluorescent vesicles are always in close contact with lysosomes, although the muscle fiber has more lysosome vesicles than LC3-RFP fluorescent vesicles. These data confirm that LC3-RFP fluorescent vesicles are indeed the indication of autophagosomes.

Autophagosome formation in G93A skeletal muscle is increased at the basal condition, but reduced following starvation.—The ALS mouse model (G93A) is asymptomatic until after 3 months of age (14). To evaluate the autophagy activity in ALS skeletal muscle during the disease progression, LC3-RFP plasmid was transfected into the FDB muscle of live G93A at different disease stages: the earlier stage (6 weeks, no axonal withdrawal reported in the G93A mice (48), 2-3 months (asymptomatic stage) and 3-4 months (disease onset) (14). Parallel experiments were also conducted in the FDB muscle of age-matched normal mice (control). The autophagosome formation was first examined in G93A and control muscles at basal condition, in which mice were kept with normal diet and no autophagy activity was induced. At this basal condition, the autophagosome formation was increased in G93A skeletal muscle at all tested age groups. It is well known that an apparent increase in autophagosome formation is not a necessary indication of increased autophage pathway or autophagy flux. It could reflect either induction of autophagy or reduced clearance of autophagosomes (40, 41, 49). Autophagy flux refers to the complete process of autophagy (40, 49). Autophagosomes are trafficked along microtubules to fuse with lysosome to form autolysosome (17). To evaluate the autophagy flux in ALS skeletal muscle, the mice were treated with colchincine, a microtubule depolymerizing agent, to block the autophagosome fusion with lysosome, a strategy established to evaluate autophagy flux in skeletal muscle (40). The starvation procedure was also applied to activate autophagy pathway. In the presence of colchincine, increased autophagosome formation induced by starvation should suggest an increased autophagy flux (40). The mice were injected (IP) with colchincine for 4 days. At day 3 of colchincine application, the mice were supplied with only water to go through the starvation procedure for 36 hours before being sacrificed for investigating the autophagosome formation. The G93A mice from three disease stages and the age-matched control mice were used for this study. As it was expected, the starvation procedure promoted autophagosome formation in skeletal muscle of normal mice at all ages, while the starvation procedure did not promote the autophagosome formation in young G93A mice, and it even reduced the autophagosome formation in G93A mice older than two months. The quantitative data is summarized in FIG. 5. These data suggest that there is an increase in autophagy activity in ALS skeletal muscle at the basal condition, while the reserved capacity to form autophagosome (the autophagy flux) in the stressed condition is largely reduced in the ALS skeletal muscle.

Figure 6:
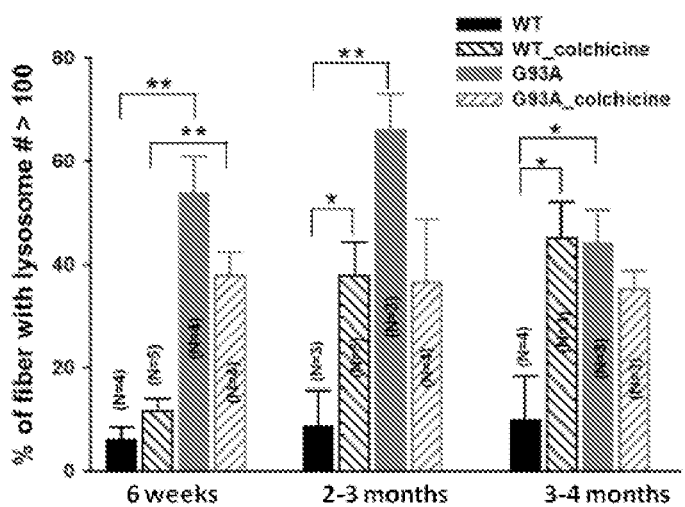
FIG. 6 illustrates quantification of lysosomes in muscle fibers at both basal and starvation conditions. Both G93A and control (WT) FDB muscle fibers were labeled with LysoTracker Green. Muscle fibers show lysosomes with various numbers. Muscle fibers were divided in 5 groups according to the number of lysosomes contained in each fibers. Quantification of lysosome activity in muscle fibers derived from three age groups at both conditions is shown. The percentage of fibers containing lysosomes more than 100 is calculated for all groups. Note, at the basal condition, G93A muscle fibers have pronounced increase in the number of lysosomes at all age groups, indicating an enhanced lysosome activity, which is in line with the increased autophagosome formation in G93A muscle at the basal condition. The muscle fibers derived from control mice responded to the starvation procedure with increased numbers of lysosomes as expected. However, the muscle fibers of G93A mice showed no increase in the numbers of lysosomes following the starvation procedure. These data are in line with the suppressed autophagy flux in G93A skeletal muscle during ALS progression.

Altered lysosome activity in skeletal muscle derived from all three age groups of G93A mice.—Autophagy is a tightly regulated cellular process that targets autophagosomes for lysosomal degradation. Thus, the lysosomal activity in G93A skeletal muscle was also examined. Lysosome vesicles were visualized by incubated live skeletal muscle fibers with LysoTrack Green. The lysosome activity was evaluated as the amount of lysosome vesicles contained in individual muscle fiber. For the convenience of the quantitative analysis, the muscle fibers were separated in 5 different groups with each containing less than 50, 50-100, 100-150, 150-200 or more than 200 lysosome vesicles respectively. The amount of lysosome vesicles are examined in skeletal muscle of G93A mice and the age-matched control mice in the basal condition and after the starvation procedure with colchincin application. The percentage of muscle fibers with lysosome vesicles more than 100 in each age group was summarized in FIG. 6. Less than 5% of control muscle fibers had more than 100 lysosome vesicles in all age groups at basal condition, indicating a quiescent lysosomal activity in normal skeletal muscle. Similar to the response of autophagosome formation, after the starvation procedure, the numbers of lysosome vesicles were significantly increased in normal muscle at all age groups. Comparing to the control, G93A muscle derived from all age groups showed significant increase in the amount of lysosome vesicles at basal condition, indicating an activated lysosome activity in G93A skeletal muscle. The G93A muscle derived from young age group (6 week) responded to the starvation procedure with further increase in lysosome vesicles, while the muscle derived from G93A mice older than 2 months had reduction in the amount of lysosome vesicles following the starvation procedure. The data suggest that the lysosome activity was altered in G93A muscle during the disease progression and those reduced lysosomal activity in the starvation condition was in line with the reduced autophagosome formation in G93A muscle at the age older than two months.

Figure 7:
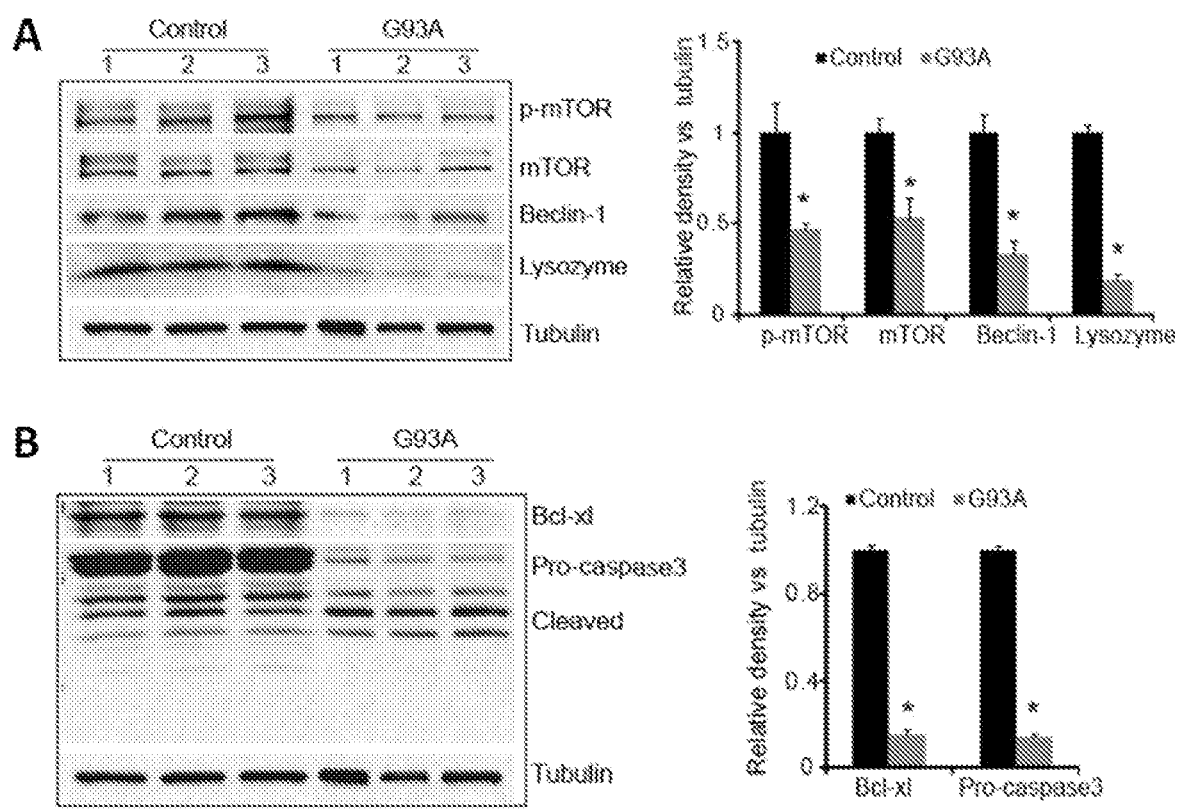
FIG. 7A-7B shows an immunoblot analysis of proteins involved in both autophagy and apoptosis pathways in skeletal muscle derived from both 3-month old G93A and control mice following the same starvation procedure. Note the pronounced reduction in the amount of proteins related to mTOR-dependent autophagy pathway. (A) The G93A muscles show decreased autophagy proteins. Right figure shows relative protein band intensity. The G93A muscles show activated apoptosis with pronounced decrease in proapoptotic protein Bcl-xl and the increase in cleaved caspase-3. Relative protein band intensity was analyzed with image/J software (NIH). (n=3 mice for control and G93A respectively, * P<0.05).

The interplay between autophagy and apoptosis pathways in G93A skeletal muscle.—The results of autophagosome formation indicated by autophage-ralated protein LC3-RFP and LysoTracker staining have suggested a suppression of autophage flux in G93A skeletal muscle during the disease progression. Autophagy flux is a dynamic, multi-step process that can be modulated at several steps (49). To further understand the molecular basis underlying this suppressed autophagy flux observed in G93A skeletal muscle, immunoblot analysis was conducted to investigate other autophagy-related proteins and pathologic changes in G93A skeletal muscle. As the reduced autophagosome formation and lysosomal activity following starvation were identified in G93A mice from 2 to 4 month older, the skeletal muscles used for immunoblot analysis were taken from 3-month old G93A mice and age-matched control mice subjected the starvation procedure described above. As illustrated in FIG. 7A, the expression level of the upstream proteins (mTOR, p-mTOR (phosphorylated-mTOR), and Beclin-1) and the downstream protein (lysozyme) (50) in autophagy pathway were significantly reduced in G93A skeletal muscle, although there was no significantly change in the ratio of p-mTOR/mTOR compared to the control muscle. The data suggest that autophagy-related proteins were likely exhausted during ALS progression, thus the G93A muscle lost the cellular machinery to further increase the autophagy flux in response to stress. We also investigated the molecular mechanism underlying this reduction in autophagy-related proteins. Autophagy is a programmed survival strategy, whereas apoptosis is programmed cell death. Accumulating evidences suggest there are interplay between those two intracellular pathways (50-52). Beclin-1 is not only an essential molecule in autophagy pathway, but also a critical component to connect autophagy and apoptosis pathways (53). Thus, the protein level of Beclin-1 in G93A muscle was examined and a dramatic reduction in G93A skeletal muscle at the stressed condition was identified (FIG. 7A). The apoptosis pathway in the same G93A skeletal muscle was investigated by examining the expression level of apoptotic markers, Bcl-xl and caspase-3, which have been shown to play a role in regulating autophagy pathway (52, 53). As shown in FIG. 7B, the expression of antiapoptotic protein Bcl-xl was dramatically decreased in G93A muscle. In addition, the G93A skeletal muscle developed a higher ratio of cleaved caspase-3 to pro-daspase-3 (FIG. 7B). This significant increase in the cleavage of caspase-3 indicates a strongly enhanced apoptosis activity in G93A skeletal muscle upon ALS progression. The data indicate that a suppressed autophagy flux is accompanied by an enhanced programmed cell death in G93A skeletal muscle and there may be a potential interplay between those two intracellular pathways during ALS progression.

Abnormal autophagy activity in skeletal muscle of an ALS mouse model in vivo has been demonstrated for the first time. Remarkably, the autophagy flux is significantly suppressed in G93A skeletal muscle upon the disease progression, although the apparent autophagosome formation seems increased at normal condition. This abnormality begins early during the disease progression and becomes severe at later stages. The reduced autophagy flux is likely due to the reduced expression level of key molecules involved in the autophagy pathway. Moreover, our study also identified a cross-talk between intracellular autophagy and apoptosis pathways in G93A skeletal muscle that likely promotes muscle atrophy and the disease progression.

It has been shown that overexpression of LC3-fluorescent protein does not affect the endogenous autophagy process (46). To assess the autophagy activity in live skeletal muscle, we chose to transfect LC3-RFP in skeletal muscle of live mice. Unlike in non-muscle cells, in which LC3-fluorescent protein distributes homogeneously inside cytosol, the expression of LC3-GFP shows striate pattern in skeletal muscle fibers, but the intracellular trafficking of LC3 protein has not been characterized (41, 46). The targeting of LC3 in skeletal muscle fibers was characterized by co-staining live muscle fibers expressing LC3-RFP with mitochondrial marker (MitoTracker Green) and lysosome marker (LysoTrack Green). The data indicate that LC3 protein evenly distributes along the Z-discs before forming vesicle-like autophagosomes in the skeletal muscle fibers.

Figure 5:
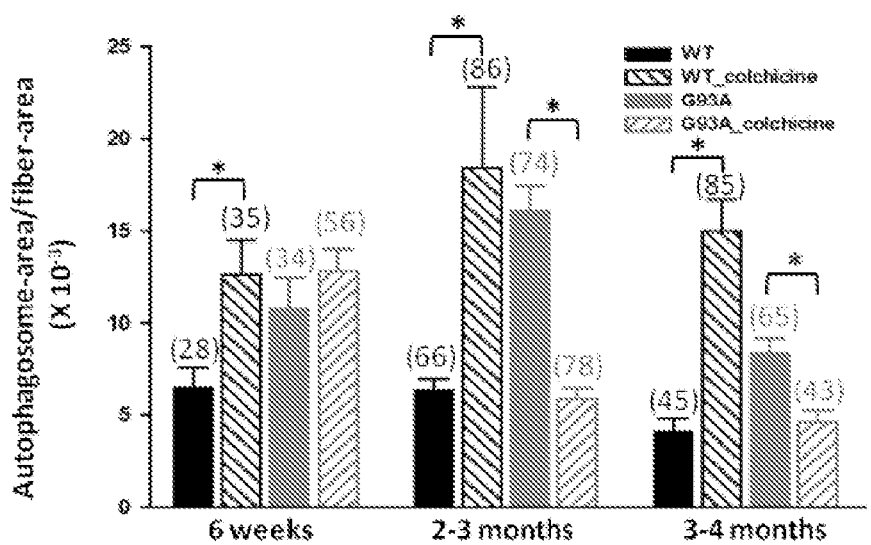
FIG. 5 illustrates the quantification of autophagosome formation in muscle fibers at both basal and starvation conditions. Both G93A and control (WT) FDB muscle fibers were transfected with LC3-RFP. Quantification of autophagosome in three age groups at both conditions. Note, at the basal condition, G93A muscle fibers show increased autophogosome formation in all age groups. While the control muscle fibers derived from all ages responded to the starvation procedure with increased autophagosome formation, the G93A muscle fibers from 6-week old mice already show no further increase in autophagosome formation, and the muscle fibers of G93A mice older than 2 months show a dramatic reduction in autophagosome formation. These data suggest that there is a suppression of autophagy flux in G93A skeletal muscle during ALS progression. Bar:10 µm.

Using LC3-RFP as an autophagosome marker, the autophagosome formation in skeletal muscle of G93A mice at three different disease stages was investigated. At the normal condition without any treatment, G93A skeletal muscle showed increased autophagosome formation indicated by increased LC3-RFP fluorescent vesicles in all three stages. These results are in line with the biochemical study reported by Crippa et al, in which they found that an increased expression level of LC3-II protein in skeletal muscle of G93A mice at the age of 2 and 4 months (22). However, it was not known if an increased expression of LC3-II was a true indication of increased autophagy activation in G93A skeletal muscle (49). Here, the autophagy flux in skeletal muscle of G93A mice was further investigated by blocking the fusion of autophagosome with lysosome while promoting autophagy by starvation, a procedure that was well established to evaluate autophagy flux in mammalian skeletal muscle (40, 41). The starvation procedure uncovered a remarkable phenomenon, in which the skeletal muscle of G93A mice showed a reduction in autophagy flux. Although there was an apparent increase in autophagosome formation at the normal condition, the young G93A mice already lost the ability to form more autophagosome vesicles in response to the starvation, and the skeletal muscle of G93A mice at the age older than 2 months even showed a significant reduction in autophagosome formation. In contrast, the skeletal muscle of normal mice responded to the starvation with a robust increase in the number of autophagosome vesicles in all age groups (FIG. 5). Thus, our data demonstrated that autophagy flux in G93A skeletal muscle was significantly suppressed, while the normal skeletal muscle show increased autophagy flux in response to the starvation as it was expected (40, 41).

There are two pathological events in skeletal muscle during ALS progression. One is the motor neuron axonal withdrawal from the neuromuscular junction leading to skeletal muscle denervation. The other is the intrinsic toxicity of mutant SOD1 protein expressed in the skeletal muscle. It has been shown that denervation induces autophagy activity in skeletal muscle (54, 55). The increased autophagy activity in the G93A skeletal muscle at normal condition could be a consequence of the motor axonal withdrawal during ALS progression. However, the early increase in autophagy activity found in the age group of 6-week old mice may have other reasons, because there is no detectable axonal withdrawal in G93A mice at this age [36]. Study by Romanello et al has shown that increased mitochondrial fission activity promoted autophagosome formation in skeletal muscle (55). Our recent study also discovered abnormal mitochondrial dynamics with increased fission activity in the skeletal muscle of G93A mice at young age and this change can be induced directly by mutant SOD1G93A protein in the absence of the axonal withdrawal (56). Thus, mutant SOD1G93A protein may play a role in promoting autophagy in G93A muscle, especially at the early stage. Indeed, the overexpression of mutant SOD1 in cultured muscle cell line C2C12 promoted autophagy activation (57). Thus, both pathological events activate autophagy in G93A muscle. This increased autophagy activity is likely a cytoprotective response of muscle cells to remove misfolded proteins and damaged organelles. However, upon the disease progression, G93A skeletal muscle lost the capacity to further activate autophagy in response to the stressed condition. Our data suggest that the autophagy-related intracellular machinery is exhausted in G93A skeletal muscle, which leads to insufficient formation of autophagosome under stressed conditions (reduced autophagy flux) to further clean up misfolded proteins. We investigated the molecular mechanism underlying this suppressed autophagy flux in G93A skeletal muscle.

The immunoblot analysis of G93A skeletal muscle was conducted to check the protein expression level of several key molecules (mTOR, Beclin-1 and lysozyme) that are involved in the mTOR-dependent autophagy pathway following the same starvation procedure. The protein expression level of those three autophagy-related molecules was dramatically reduced in G93A muscle at the age of 3 months as described herein. The result is in line with the reduced autophagosome formation observed by overexpression of LC3-RFP in live G93A skeletal muscle at the same starvation condition. mTOR, an upstream molecule in mTOR-dependent autophagy pathway, is a negative regulator of autophagy activity. In a nutrient-rich environment, mTOR is activated by phosphorylation to suppress autophagy, while in a nutrient-depleted environment, mTOR is inhibited, which leads to activation of the autophagy pathway (58). A reduced ratio of p-mTOR/mTOR is an indication of activation of autophagy (21). We examined the expression level of both p-mTOR and mTOR in G93A muscle and found no significant changes in the ratio of p-mTOR/mTOR, but a dramatic reduction on the protein level of total mTOR (including both p-mTOR and mTOR) when compared to the normal control muscle. It has been shown that there is a reduced expression of mTOR in the skeletal muscle of transgenic mice with restricted-muscle overexpression of SOD1G93A (59), suggesting the accumulation of mutant SOD1 protein could lead to reduced expression of mTOR in skeletal muscle. The transgenic ALS mouse model G93A systematically expresses mutant SOD1G93A (14) and our study also showed high expression level of SOD1G93A in skeletal muscle of G93A mice (56). The results indicate that accumulation of mutant SOD1G93A may be one of the reasons for the reduced expression of mTOR in the skeletal muscle of G93A mice, although the detailed mechanism remains unclear.

Figure 8:
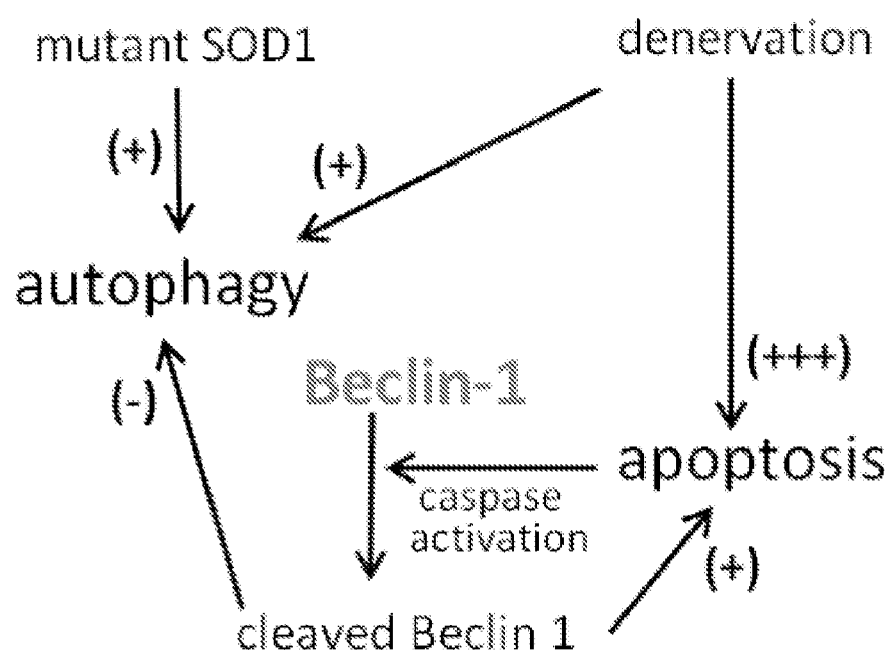
FIG. 8 illustrates proposed pathogenic sequences in muscle of the ALS model. During ALS progression, both accumulation of mutant SOD1 protein and motor axonal withdrawal could promote muscle autophagy, a cytoprotective process. At later stage, axonal withdrawal becomes not compensable and triggers apoptosis, which leads to capases-mediated cleavage of autophagy-related proteins, especially Beclin-1. The cleavage of Beclin-1 inhibits autophagy pathway and further promotes apoptosis. This disturbed interplay between autophagy and apoptosis forms a vicious cycle that could lead to devastating muscle degeneration and promote disease progression.

Apoptosis activity was also examined in the same G93A muscle. Apoptosis is another important signal pathways involved in skeletal muscle atrophy at various pathophysiological conditions. Activation of apoptosis pathway has been demonstrated in skeletal muscle following denervation (50, 51). Increased apoptosis activity has been seen in the skeletal muscle of ALS patients (62, 63) and ALS mouse model G93A with upregulated caspase activity (59, 64). In line with those findings, this study also identified upregulated apoptosis activity in G93A skeletal muscle evident with reduced Bcl-xl protein and increase in cleaved caspase-3. Notably, the upregulated apoptosis activity is companied with the reduced autophagy flux in the skeletal muscle of G93A mice. The mechanisms linking autophagy and apoptosis are not fully defined. Beclin-1 was examined in G93A muscle and a dramatic reduction in its expression level following the same starvation procedure was identified. Studies have shown that caspase-mediated cleavage of Beclin-1 inactivates autophagy and enhances apoptosis (65, 66). Thus, cleavage of Beclin-1 initiated by apoptosis is likely a critical component leading to the suppressed autophagy flux observed in G93A skeletal muscle. Based on past and present results, one potential pathogenic sequence in ALS skeletal muscle is depicted in FIG. 8. In early stages, the accumulation of mutant SOD1 inside mitochondria may play a major role in activating autophagy pathway. Upon the disease progression, motor neuron withdrawal also triggers autophagy in G93A skeletal muscle. Thus, an apparent increase in autophagosome formation was observed in all stages of G93A skeletal muscle. However, when axonal withdrawal becomes not compensable, the severe denervation promotes apoptosis pathway rigorously especially at stressed circumstances. Apoptosis activates caspases, which leads to cleavage of autophagy-related proteins, especially Beclin-1. The cleaved Beclin-1 inactivates autophagy but further enhances apoptosis in the G93A muscle [38, 41]. Autophagy is considered as a cytoprotective pathway that cleans up aged organelles and misfolded proteins and provides nutrients to important organs in the stressed condition, while apoptosis is a process of programmed cell death. In the course of ALS progression, the motor axonal withdrawal activates apoptosis pathway and initiates caspase-mediated cleavage of Beclin-1, which would further promotes a vicious cycle of apoptosis and suppresses the cytoprotective autophagy pathway. This unbalanced cross-talk between autophagy and apoptosis could exacerbate the skeletal muscle atrophy during ALS progression, especially at later stages.

As shown, the autophagy flux in G93A skeletal muscle is significantly suppressed upon ALS progression. This suppression is likely due to the activation of apoptosis induced by motor axonal withdrawal, which could lead to the cleavage of autophagy-related key proteins. Among them, the cleaved Beclin-1 may play an essential role in shifting the cytoprotective autophagy response to cell-death apoptosis response, which exacerbates skeletal muscle atrophy during ALS progression. Importantly, this study provides a new clue that may explain the contradictory outcomes of treating ALS by targeting the upstream molecular mTOR.

Experimental Procedures

Gene transfection in skeletal muscle of adult mice.—G93A (14) and the age matched normal (wide type) mice were used in this study. Transfection was done using an electroporation protocol that was modified from (42) and (43). Briefly, anaesthetized mice were injected with 10 µl of 2 mg/ml hyaluronidase dissolved in sterile saline at the ventral side of their hind paws using a 29-gauge needle. One hour later, 5-10 µg plasmid DNA (pcDNA3/LC3-RFP) in 10 µl sterile saline was injected at the same sites. Fifteen minutes later, two electrodes (gold plated stainless steel acupuncture needles) ~9 mm apart were placed at the starting lines of paw and toes. Twenty pulses of 100 V/cm at 20 ms/pulse were applied at 1 Hz (ECM 830 Electro Square Porator, BTX). Seven days later, the animal was euthanized by CO2 inhalation and the flexor digitorum brevis (FDB) muscles were removed for functional studies. All experiments were carried out in strict accordance with the recommendation in the Guide for the Care and Use of Laboratory Animals of the National Institutes of Health. All experimental protocols were approved by the IACUC of Rush University.

Muscle fiber preparation.—Individual muscle fibers were isolated following a protocol described previously (43, 44). FDB muscles were digested in modified Krebs solution (0 Ca2+) plus 0.2% type I collagenase for 55 min at 37° C. Following this collagenase treatment, muscle fibers were stored in an enzyme-free Krebs solution at 4° C., and used for imaging studies within 24 hours.

Fluorescent dye loading and confocal microscopic imaging.—FDB muscle fibers were incubated with 200 nM MitoTracker Green for 30 min at 25° C. to visualize mitochondria and 500 nM LysoTracker Green 15 min at 25° C. t0 visualize lysosomes. In some cases, images of MitoTracker Green or LysoTracker Green signals were simultaneously recorded with LC3-RFP. MitoTracker Green or LysoTracker Green was excited at 488 nm and its emitted fluorescence was collected at 490-540. LC3-RFP was excited at 543 and its emitted fluorescence was collected at 560-620. A confocal microscope (SP2-AOBS Leica Microsystem, Gemany with a 63X, 1.2 NA water-immersion objective) capable of line-interleaving images excited with different lasers, was used. Both MitoTracker Green and LysoTracker Green were purchased from Invitrogen.

Pharmacological reagents and starvation protocol. A modified starvation procedure was applied to examine autophagy flux (40). Colchincine was applied by intraperitoneal injection at a dose of 0.4 mg/kg/day for 4 days. On the 3rd day, the mice were put into a new cage and supplied only with water, initiating a 36 hours starvation period. After this starvation period, FDB muscles were removed for examination of autophagosome formation and immunoblotting analysis. Colchincine was dissolved in deionized water at 4 mg/ml. Then 20 μl colchincine (80 μg) solution was dissolved in 800 μl saline for intraperitoneal injection. Colchincine and other chemicals were obtained from Sigma.

Immunoblot Assay.—Tibialis anterior muscles from normal and G93A mice were collected and homogenized in protein extraction buffer containing protease inhibitor cocktail (Thermo Scientific) using motorized homogenizer (Wheaton). Protein concentrations were determined by BCA protein assay (Thermo Scientific). Equal amount of protein samples (~30 μg) were subjected to SDS-polyacrylamide gel electrophoresis before being transferred to nitrocellulose (Bio-Rad, Hercules, Calif.) and immunoblotted with primary antibodies. The antibodies used were: anti-phospho-mTOR (ser2448) (Cell Signaling, 5536), anti-mTOR (Cell Signaling, 2983), anti-LC3 (Cell Signaling, 2775), anti-caspase-3 (Cell Signaling, 9665), anti-VPS34 (Invitrogen, 382100), anti-Beclin 1 (Santa Cruz, sc-10086), anti-P53 (Santa Cruz, sc-126), anti-Bcl-xl (Santa Cruz, sc-8392). All these antibodies were used at a 1:1000 dilution. One antibody, anti-tubulin (Santa Cruz Biotechnology) was used at a 1:10000 dilution. Results were visualized with ECL reagents (Thermo). Densitometry evaluation was conducted using Image/J software (NIH).

Image processing and data analysis.—IDL 7.0 (IDL, ITT Visual Information Solutions) was used for image processing. Sigmaplot 11.0 and Microsoft Excel were used for data analysis. Data are represented as mean±S.E.M. Statistical significance was determined by Student's t test.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. Alonso A1, Logroscino G, Jick S S, Hernán M A. (2009). Incidence and lifetime risk of motor neuron disease in the United Kingdom: a population-based study. Eur J Neurol. 16(6):745-51.
2. McGoldrick P1, Joyce P I, Fisher E M, Greensmith L. (2013). Rodent models of amyotrophic lateral sclerosis. Biochim Biophys Acta. 1832(9):1421-36. doi: 10.1016
3. Joyce P I1, Fratta P, Fisher E M, Acevedo-Arozena A. (2011). SOD1 and TDP-43 animal models of amyotrophic lateral sclerosis: recent advances in understanding disease toward the development of clinical treatments. Mamm Genome. 22(7-8):420-48. doi: 10.1007/s00335-011-9339-1.
4. NIH: ALS fact sheet: http://www.ninds.nih.gov/disorders/amyotrophiclateralsclerosis/detail_ALS.htm
5. The ALS association: http://www.alsa.org/
6. Littman D R, Pamer E G. (2011). Role of the commensal microbiota in normal and pathogenic host immune responses. Cell host & microbe 10:311-23.
7. Mshvildadze M, Neu J. The infant intestinal microbiome: Friend or foe? Early Hum Dev.
8. Hooper LV. Do symbiotic bacteria subvert host immunity? Nat Rev Microbiol 2009; 7:367-74.
9. Hooper L V, Midtvedt T, Gordon J I. How host-microbial interactions shape the nutrient environment of the mammalian intestine. Annu Rev Nutr 2002; 22:283-307.
10. Xu Z, Shen F, Li X, Wu Y, Chen Q, Jie X, Yao M. Molecular and microscopic analysis of bacteria and viruses in exhaled breath collected using a simple impaction and condensing method. PLoS One 2012; 7:e41137.
11. Lu R, Wu S, Liu X, et al. Chronic effects of a Salmonella type III secretion effector protein AvrA in vivo. *PLoS One* 2010; 5:e10505.
12. Cadwell K, Liu J Y, Brown S L, et al. A key role for autophagy and the autophagy gene Atg16I1 in mouse and human intestinal Paneth cells. *Nature* 2008; 456:259-63.
13. Pasinelli P, Brown R H (2006) Molecular biology of amyotrophic lateral sclerosis: insights from genetics. Nat Rev Neurosci 7: 710-723. doi:10.1038/nrn1971.
14. Gurney M E, Pu H, Chiu A Y, Dal Canto M C, Polchow C Y, et al. (1994) Motor neuron degeneration in mice that express a human Cu,Zn superoxide dismutase mutation. Science 264: 1772-1775.
15. Nassif M, Hetz C (2011) Targeting autophagy in ALS: a complex mission. Autophagy 7: 450-453.
16. Mizushima N (2007) Autophagy: process and function. Genes Dev 21: 2861-2873. doi:10.1101/gad.1599207.
17. Banerjee R, Beal M F, Thomas B (2010) Autophagy in neurodegenerative disorders: pathogenic roles and therapeutic implications. Trends Neurosci 33: 541-549. doi: 10.1016/j.tins.2010.09.001.
18. Li L, Zhang X, Le W (2008) Altered macroautophagy in the spinal cord of SOD1 mutant mice. Autophagy 4: 290-293.
19. Morimoto N, Nagai M, Ohta Y, Miyazaki K, Kurata T, et al. (2007) Increased autophagy in transgenic mice with a G93A mutant SOD1 gene. Brain Res 1167: 112-117. doi:10.1016/j.brainres.2007.06.045.
20. Sasaki S (2011) Autophagy in spinal cord motor neurons in sporadic amyotrophic lateral sclerosis. J Neuropathol Exp Neurol 70: 349-359. doi:10.1097/NEN.0b013e3182160690.
21. Zhang X, Li L, Chen S, Yang D, Wang Y, et al. (2011) Rapamycin treatment augments motor neuron degeneration in SOD1(G93A) mouse model of amyotrophic lateral sclerosis. Autophagy 7: 412-425.
22. Crippa V, Boncoraglio A, Galbiati M, Aggarwal T, Rusmini P, et al. (2013) Differential autophagy power in the spinal cord and muscle of transgenic ALS mice. Front Cell Neurosci 7: 234. doi:10.3389/fncel.2013.00234.
23. Hetz C, Thielen P, Matus S, Nassif M, Court F, et al. (2009) XBP-1 deficiency in the nervous system protects against amyotrophic lateral sclerosis by increasing autophagy. Genes Dev 23: 2294-2306. doi:10.1101/gad.1830709.
24. Ikenaka K, Kawai K, Katsuno M, Huang Z, Jiang Y-M, et al. (2013) dnc-1/dynactin 1 knockdown disrupts transport of autophagosomes and induces motor neuron degeneration. PloS One 8: e54511. doi:10.1371/journal.pone.0054511.
25. Bové J, Martinez-Vicente M, Vila M (2011) Fighting neurodegeneration with rapamycin: mechanistic insights. Nat Rev Neurosci 12: 437-452. doi:10.1038/nrn3068.

26. Chen S, Zhang X, Song L, Le W (2012) Autophagy dysregulation in amyotrophic lateral sclerosis. Brain Pathol Zurich Switz 22: 110-116. doi:10.1111/j.1750-3639.2011.00546.x.
27. Wang I-F, Guo B-S, Liu Y-C, Wu C-C, Yang C-H, et al. (2012) Autophagy activators rescue and alleviate pathogenesis of a mouse model with proteinopathies of the TAR DNA-binding protein 43. Proc Natl Acad Sci USA 109: 15024-15029. doi:10.1073/pnas.1206362109.
28. Bhattacharya A, Bokov A, Muller F L, Jernigan A L, Maslin K, et al. (2012) Dietary restriction but not rapamycin extends disease onset and survival of the H46R/H48Q mouse model of ALS. Neurobiol Aging 33: 1829-1832. doi:10.1016/j.neurobiolaging.2011.06.002.
29. Fornai F, Longone P, Cafaro L, Kastsiuchenka O, Ferrucci M, et al. (2008) Lithium delays progression of amyotrophic lateral sclerosis. Proc Natl Acad Sci USA 105: 2052-2057. doi:10.1073/pnas.0708022105.
30. Pizzasegola C, Caron I, Daleno C, Ronchi A, Minoia C, et al. (2009) Treatment with lithium carbonate does not improve disease progression in two different strains of SOD1 mutant mice. Amyotroph Lateral Scler Off Publ World Fed Neurol Res Group Mot Neuron Dis 10: 221-228. doi:10.1080/17482960902803440.
31. Boillée S, Vande Velde C, Cleveland D W (2006) ALS: a disease of motor neurons and their nonneuronal neighbors. Neuron 52: 39-59. doi:10.1016/j.neuron.2006.09.018.
32. Neel B A, Lin Y, Pessin J E (2013) Skeletal muscle autophagy: a new metabolic regulator. Trends Endocrinol Metab TEM 24: 635-643. doi:10.1016/j.tem.2013.09.004.
33. Dobrowolny G, Giacinti C, Pelosi L, Nicoletti C, Winn N, et al. (2005) Muscle expression of a local Igf-1 isoform protects motor neurons in an ALS mouse model. J Cell Biol 168: 193-199. doi:10.1083/jcb.200407021.
34. Nguyen Q T, Son Y J, Sanes J R, Lichtman J W (2000) Nerve terminals form but fail to mature when postsynaptic differentiation is blocked: in vivo analysis using mammalian nerve-muscle chimeras. J Neurosci Off J Soc Neurosci 20: 6077-6086.
35. Dobrowolny G, Aucello M, Rizzuto E, Beccafico S, Mammucari C, et al. (2008) Skeletal muscle is a primary target of SOD1G93A-mediated toxicity. Cell Metab 8: 425-436. doi:10.1016/j.cmet.2008.09.002.
36. Wong M, Martin L J (2010) Skeletal muscle-restricted expression of human SOD1 causes motor neuron degeneration in transgenic mice. Hum Mol Genet 19: 2284-2302. doi:10.1093/hmg/ddq106.
37. Miller T M, Kim S H, Yamanaka K, Hester M, Umapathi P, et al. (2006) Gene transfer demonstrates that muscle is not a primary target for non-cell-autonomous toxicity in familial amyotrophic lateral sclerosis. Proc Natl Acad Sci USA 103: 19546-19551. doi:10.1073/pnas.0609411103.
38. Grumati P, Coletto L, Sabatelli P, Cescon M, Angelin A, et al. (2010) Autophagy is defective in collagen VI muscular dystrophies, and its reactivation rescues myofiber degeneration. Nat Med 16: 1313-1320. doi:10.1038/nm.2247.
39. Pauly M, Daussin F, Burelle Y, Li T, Godin R, et al. (2012) AMPK activation stimulates autophagy and ameliorates muscular dystrophy in the mdx mouse diaphragm. Am J Pathol 181: 583-592. doi:10.1016/j.ajpath.2012.04.004.
40. Ju J-S, Varadhachary A S, Miller S E, Weihl C C (2010) Quantitation of "autophagic flux" in mature skeletal muscle. Autophagy 6: 929-935. doi:10.4161/auto.6.7.12785.
41. Mammucari C, Milan G, Romanello V, Masiero E, Rudolf R, et al. (2007) FoxO3 controls autophagy in skeletal muscle in vivo. Cell Metab 6: 458-471. doi:10.1016/j.cmet.2007.11.001.
42. Pouvreau S, Royer L, Yi J, Brum G, Meissner G, et al. (2007) Ca(2+) sparks operated by membrane depolarization require isoform 3 ryanodine receptor channels in skeletal muscle. Proc Natl Acad Sci USA 104: 5235-5240. doi:10.1073/pnas.0700748104.
43. Zhou J, Yi J, Fu R, Liu E, Siddique T, et al. (2010) Hyperactive intracellular calcium signaling associated with localized mitochondrial defects in skeletal muscle of an animal model of amyotrophic lateral sclerosis. J Biol Chem 285: 705-712. doi:10.1074/jbc.M109.041319.
44. Yi J, Ma C, Li Y, Weisleder N, Rios E, et al. (2011) Mitochondrial calcium uptake regulates rapid calcium transients in skeletal muscle during excitation-contraction (E-C) coupling. J Biol Chem 286: 32436-32443. doi:10.1074/jbc.M110.217711.
45. Kabeya Y, Mizushima N, Ueno T, Yamamoto A, Kirisako T, et al. (2000) LC3, a mammalian homologue of yeast Apg8p, is localized in autophagosome membranes after processing. EMBO J 19: 5720-5728. doi:10.1093/emboj/19.21.5720.
46. Mizushima N, Yamamoto A, Matsui M, Yoshimori T, Ohsumi Y (2004) In vivo analysis of autophagy in response to nutrient starvation using transgenic mice expressing a fluorescent autophagosome marker. Mol Biol Cell 15: 1101-1111. doi:10.1091/mbc.E03-09-0704.
47. Boncompagni S, Rossi A E, Micaroni M, Beznoussenko G V, Polishchuk R S, et al. (2009) Mitochondria are linked to calcium stores in striated muscle by developmentally regulated tethering structures. Mol Biol Cell 20: 1058-1067. doi:10.1091/mbc.E08-07-0783.
48. Frey D, Schneider C, Xu L, Borg J, Spooren W, et al. (2000) Early and selective loss of neuromuscular synapse subtypes with low sprouting competence in motoneuron diseases. J Neurosci Off J Soc Neurosci 20: 2534-2542.
49. Klionsky D J, Abeliovich H, Agostinis P, Agrawal D K, Aliev G, et al. (2008) Guidelines for the use and interpretation of assays for monitoring autophagy in higher eukaryotes. Autophagy 4: 151-175.
50. Marino G, Niso-Santano M, Baehrecke E H, Kroemer G (2014) Self-consumption: the interplay of autophagy and apoptosis. Nat Rev Mol Cell Biol. doi:10.1038/nrm3735.
51. Maiuri M C, Criollo A, Kroemer G (2010) Crosstalk between apoptosis and autophagy within the Beclin 1 interactome. EMBO J 29: 515-516. doi:10.1038/emboj.2009.377.
52. Mukhopadhyay S, Panda P K, Sinha N, Das D N, Bhutia S K (2014) Autophagy and apoptosis: where do they meet? Apoptosis Int J Program Cell Death. doi:10.1007/s10495-014-0967-2.
53. Djavaheri-Mergny M, Maiuri M C, Kroemer G (2010) Cross talk between apoptosis and autophagy by caspase-mediated cleavage of Beclin 1. Oncogene 29: 1717-1719. doi:10.1038/onc.2009.519.
54. O'Leary M F N, Vainshtein A, Carter H N, Zhang Y, Hood D A (2012) Denervation-induced mitochondrial dysfunction and autophagy in skeletal muscle of apoptosis-deficient animals. Am J Physiol Cell Physiol 303: C447-454. doi:10.115$^2$/ajpcell.00451.2011.
55. Romanello V, Guadagnin E, Gomes L, Roder I, Sandri C, et al. (2010) Mitochondrial fission and remodelling contributes to muscle atrophy. EMBO J 29: 1774-1785. doi:10.1038/emboj.2010.60.

56. Luo G, Yi J, Ma C, Xiao Y, Yi F, et al. (2013) Defective mitochondrial dynamics is an early event in skeletal muscle of an amyotrophic lateral sclerosis mouse model. PloS One 8: e82112. doi:10.1371/journal.pone.0082112.
57. Onesto E, Rusmini P, Crippa V, Ferri N, Zito A, et al. (2011) Muscle cells and motoneurons differentially remove mutant SOD1 causing familial amyotrophic lateral sclerosis. J Neurochem 118: 266-280. doi:10.1111/j.1471-4159.2011.07298.x.
58. Díaz-Troya S, Pérez-Pérez M E, Florencio F J, Crespo J L (2008) The role of TOR in autophagy regulation from yeast to plants and mammals. Autophagy 4: 851-865.
59. Dobrowolny G, Aucello M, Musarò A (2011) Muscle atrophy induced by SOD1G93A expression does not involve the activation of caspase in the absence of denervation. Skelet Muscle 1: 3. doi:10.1186/2044-5040-1-3.
60. Siu P M, Alway S E (2005) Mitochondria-associated apoptotic signalling in denervated rat skeletal muscle. J Physiol 565: 309-323. doi:10.1113/jphysiol.2004.081083.
61. Adhihetty P J, O'Leary M F N, Chabi B, Wicks K L, Hood D A (2007) Effect of denervation on mitochondrially mediated apoptosis in skeletal muscle. J Appl Physiol 102: 1143-1151. doi:10.1152/japplphysiol.00768.2006.
62. Tews D S, Goebel H H, Meinck H M (1997) DNA-fragmentation and apoptosis-related proteins of muscle cells in motor neuron disorders. Acta Neurol Scand 96: 380-386.
63. Schoser B G, Wehling S, Blottner D (2001) Cell death and apoptosis-related proteins in muscle biopsies of sporadic amyotrophic lateral sclerosis and polyneuropathy. Muscle Nerve 24: 1083-1089.
64. Kaspar B K, Lladó J, Sherkat N, Rothstein J D, Gage F H (2003) Retrograde Viral Delivery of IGF-1 Prolongs Survival in a Mouse ALS Model. Science 301: 839-842. doi:10.1126/science.1086137.
65. Luo S, Rubinsztein D C (2010) Apoptosis blocks Beclin 1-dependent autophagosome synthesis: an effect rescued by Bcl-xL. Cell Death Differ 17: 268-277. doi:10.1038/cdd.2009.121.
66. Wirawan E, Vande Walle L, Kersse K, Cornelis S, Claerhout S, et al. (2010) Caspase-mediated cleavage of Beclin-1 inactivates Beclin-1-induced autophagy and enhances apoptosis by promoting the release of proapoptotic factors from mitochondria. Cell Death Dis 1: e18. doi:10.1038/cddis.2009.16.
67. Blikslager, A. T., A. J. Moeser, J. L. Gookin, S. L. Jones, and J. Odle. 2007. Restoration of barrier function in injured intestinal mucosa. Physiol. Ref. 87:545-564.
68. Collins, S. M., and P. Bercik. 2009. The relationship between intestinal microbiota and the central nervous system in normal gastrointestinal function and disease. Gastroenterology 136:2003-2014.
69. Deng, H. X., Y. Shi, Y. Furukawa, H. Zhai, R. Fu, E. Liu, et al. 2006. Conversion to the amyotrophic lateral sclerosis phenotype is associated with intermolecular linked insoluble aggregates of SOD1 in mitochondria. Proc. Natl Acad. Sci. USA 103:7142-7147.
70. Farhadi, A., A. Banan, J. Fields, and A. Keshavarzian. 2003. Intestinal barrier: an interface between health and disease. J. Gastroenterol. Hepatol. 18:479-497.
71. Finegold, S. M., S. E. Dowd, V. Gontcharova, C. Liu, K. E. Henley, R. D. Wolcott, et al. 2010. Pyrosequencing study of fecal microflora of autistic and control children. Anaerobe 16:444-453.
72. Hsiao, E. Y., S. W. McBride, S. Hsien, G. Sharon, E. R. Hyde, T. McCue, et al. 2013. Microbiota modulate behavioral and physiological abnormalities associated with neurodevelopmental disorders. Cell 155:1451-1463.
73. Ivanova, M. I., S. A. Sievers, E. L. Guenther, L. M. Johnson, D. D. Winkler, A. Galaleldeen, et al. 2014. Aggregation-triggering segments of SOD1 fibril formation support a common pathway for familial and sporadic ALS. Proc. Natl Acad. Sci. USA 111:197-201.
74. Kim, J., H. Lee, J. H. Lee, D. Y. Kwon, A. Genovesio, D. Fenistein, et al. 2014. Dimerization, oligomerization, and aggregation of human amyotrophic lateral sclerosis Cu/Zn-superoxide dismutase 1 mutant forms in live cells. J. Biol. Chem. 289:15094-15103.
75. Klionsky, D. J., H. Abeliovich, P. Agostinis, D. K. Agrawal, G. Aliev, D. S. Askew, et al. 2008. Guidelines for the use and interpretation of assays for monitoring autophagy in higher eukaryotes. Autophagy 4:151-175.
76. Laukoetter, M. G., P. Nava, W. Y. Lee, E. A. Severson, C. T. Capaldo, B. A. Babbin, et al. 2007. JAM-A regulates permeability and inflammation in the intestine in vivo. J. Exp. Med. 204:3067-3076.
77. Lee, H. E. H. Ko, M. Lai, N. Wei, J. Balroop, Z. Kashem, et al. 2014. Delineating the relationships among the formation of reactive oxygen species, cell membrane instability and innate autoimmunity in intestinal reperfusion injury. Mol. Immunol. 58(2):151-159.
78. Ling, J., Liao, R. Clark, M. S. Wong, and D. D. Lo. 2008. Structural constraints for the binding of short peptides to claudin-4 revealed by surface plasmon resonance. J. Biol. Chem. 283:30585-30595.
79. Maes, M. M. Kubera, and J. C. Leunis. 2008. The gut-brain barrier in major depression: intestinal mucosal dysfunction with an increased translocation of LPS from gram negative enterobacteria (leaky gut) plays a role in the inflammatory pathophysiology of depression. Neuro Endocrinol. Lett. 29:117-124.
80. McCombe, P. A., and R. D. Henderson. 2011. The Role of immune and inflammatory mechanisms in ALS. Curr. Mol. Med. 11:246-254.
81. Murrow, L., and J. Debnath. 2013. Autophagy as a stress-response and quality-control mechanism: implications for cell injury and human disease. Annu. Rev. Pathol. 8:105-137.
82. Phan, T. G., J. A. Green, E. E. Gray, Y. Xu, and J. G. Cyster. 2009. Immune complex relay by subcapsular sinus macrophages and noncognate B cells drives antibody affinity maturation. Nat. Immunol. 10:786-793.
83. Rajapaksa, T. E., M. Stover-Hamer, X. Fernandez, H. A. Eckelhoefer, and D. D. Lo. 2010. Claudin 4-targeted protein incorporated into PLGA nanoparticles can mediate M cell targeted delivery. J. Control. Release 142:196-205.
84. Sasaki, S. 2011. Autophagy in spinal cord motor neurons in sporadic amyotrophic lateral sclerosis. J. Neuropathol. Exp. Neurol. 70:349-359.
85. Schulz, M. D., C. Atay, J. Heringer, F. K. Romrig, S. Schwitalla, B. Aydin, et al. 2014. High-fat-diet-mediated dysbiosis promotes intestinal carcinogenesis independently of obesity. Nature 514:608-512.
86. Shen, L., and J. R. Turner. 2006. Role of epithelial cells in initiation and propagation of intestinal inflammation. Eliminating the static: tight junction dynamics exposed. Am. J. Physiol. Gastrointest. Liver Physiol. 290:G577-G582.

87. Sun, J., and B. E. Chang. 2014. Exploring gut microbes in human health and disease: pushing the envelope. Genes Dis. 1:132-139.
88. Takahashi, N., I. Vanlaere, R. de Rycke, A. Cauwels, L. A. Joosten, E. Lubberts, et al. 2008. IL-17 produced by Paneth cells drives TNF-induced shock. J. Exp. Med. 205:1755-1761.
89. Virgin, H. W., and B. Levin. 2009. Autophagy genes in immunity. Nat. Immunol. 10:461-470.
90. Xiao, Y., C. Ma, S. Wu, S. J. Yi, P. Lin, J. Sun, et al. 2015. Suppressed autophagy flux in skeletal muscle of an amyotrophic lateral sclerosis mouse model upon disease progression. Physiol. Rep. 3:e12271.
91. Yuk, J. M., T. Yoshimori, and E. K. Jo. 2012. Autophagy and bacterial infectious diseases. Exp. Mol. Med. 44:99-108.
92. Zhang, X., S. Chen, L. Song, Y. Tang, Y. Shen, L. Jia, et al. 2014. MTOR-independent, autophagic enhancer trehalose prolongs motor neuron survival and ameliorates the autophagic flux defect in a mouse model of amyotrophic lateral sclerosis. Autophagy 10:588-602.

The invention claimed is:

1. A method of identifying an asymptomatic subject for stratification into an amyotrophic lateral sclerosis (ALS) treatment regime, the method comprising:
obtaining a biological sample from the subject, wherein the sample is obtained from the subject's gastrointestinal tract;
a) measuring a level of a microbial population and detecting whether there is a change in the microbial population in the gastrointestinal tract relative to a control subject;
b) measuring a level of a microbial marker and detecting whether there is a change in the microbial marker in the gastrointestinal tract relative to a control subject;
c) measuring a level of a tight junction marker and detecting whether there is a loss of structure and function in the gastrointestinal tract relative to a control subject; and
d) measuring a level of a Paneth cell defect and detecting whether there is a change in a number of Paneth cells/crypt or a change in a number of abnormal cells in the gastrointestinal tract relative to a control subject; and
identifying the subject having each of the decrease in a), the decrease in b), the loss of structure and function in c) and the decrease in the number of Paneth cells/crypt or the increase in the number of abnormal cells in d).

2. The method according to claim 1, wherein the microbial population is selected from the group consisting of *Butyivibrio fibrosolvens, Firmicutes peptostreptococcus, Escherichia coli* and combinations thereof.

3. The method according to claim 1, wherein the microbial marker comprises butyryl-coenzyme A CoA transferase or defensins.

4. The method according to claim 1, wherein the tight junction marker comprises ZO-1 or Claudin2.

5. The method according to claim 1, further comprising measuring an expression level of one or more apoptosis or autophagy pathway biomarkers.

6. The method according to claim 5, comprising measuring an mTOR-dependent autophagy pathway biomarker.

7. The method according to claim 5, comprising measuring one or more of p-mTOR, mTOR, Beclin-1, and lysozyme.

8. The method according to claim 5, comprising measuring an expression level of Bcl-xl or Pro-caspase 3.

9. The method according to claim 5, wherein the autophagy activity is measured in the gastrointestinal tract or skeletal muscle.

10. The method according to claim 1, comprising measuring the level in a fecal sample or a mucosal sample.

11. The method according to claim 1, wherein the microbial population is selected from the group consisting of *Butyivibrio fibrosolvens, Firmicutes peptostreptococcus, Escherichia coli* and combinations thereof and the microbial marker comprises butyryl-coenzyme A CoA transferase or defensins.

12. The method according to claim 1, wherein the microbial population is selected from the group consisting of *Butyivibrio fibrosolvens, Firmicutes peptostreptococcus, Escherichia coli* and combinations thereof and the tight junction marker comprises ZO-1 or Claudin2.

13. The method according to claim 1, wherein the microbial population is selected from the group consisting of *Butyivibrio fibrosolvens, Firmicutes peptostreptococcus, Escherichia coli* and combinations thereof; the microbial marker comprises butyryl-coenzyme A CoA transferase or defensins; and the tight junction marker comprises ZO-1 or Claudin2.

14. The method according to claim 1, wherein the microbial marker comprises butyryl-coenzyme A CoA transferase or defensins and the tight junction marker comprises ZO-1 or Claudin2.

* * * * *